(12) United States Patent
Lavania et al.

(10) Patent No.: US 11,874,100 B2
(45) Date of Patent: Jan. 16, 2024

(54) DEVICE AND METHOD FOR CONTROLLED EMISSION OF RADIATION

(71) Applicants: Anupam Lavania, Gujarat (IN); Shilpa Malik, Gujarat (IN)

(72) Inventors: Anupam Lavania, Gujarat (IN); Shilpa Malik, Gujarat (IN)

(*) Notice: Subject to any disclaimer, the term of this patent is extended or adjusted under 35 U.S.C. 154(b) by 495 days.

(21) Appl. No.: 17/275,485

(22) PCT Filed: Sep. 12, 2019

(86) PCT No.: PCT/IB2019/057706
§ 371 (c)(1),
(2) Date: Mar. 11, 2021

(87) PCT Pub. No.: WO2020/053810
PCT Pub. Date: Mar. 19, 2020

(65) Prior Publication Data
US 2022/0034649 A1 Feb. 3, 2022

(30) Foreign Application Priority Data
Sep. 12, 2018 (IN) .............................. 201821034397

(51) Int. Cl.
*G01L 1/04* (2006.01)
*G01B 11/14* (2006.01)
*G01B 17/00* (2006.01)
(52) U.S. Cl.
CPC .............. *G01B 11/14* (2013.01); *G01B 17/00* (2013.01); *G01L 1/04* (2013.01)
(58) Field of Classification Search
CPC ............ G01B 11/14; G01B 17/00; G01L 1/04

USPC .......................................................... 73/1.1
See application file for complete search history.

(56) References Cited

U.S. PATENT DOCUMENTS

| 3,941,670 | A | * | 3/1976 | Pratt, Jr. .................. | A23L 3/26 250/423 P |
| 10,448,997 | B2 | * | 10/2019 | Palero .................. | A61B 5/0059 |
| 2008/0004611 | A1 | * | 1/2008 | Houbolt ................ | A61B 5/443 606/9 |
| 2008/0221409 | A1 | * | 9/2008 | Hoarau ................ | A61B 5/4872 600/12 |
| 2014/0107638 | A1 | * | 4/2014 | Hancock ................ | A61B 18/18 606/33 |

(Continued)

*Primary Examiner* — Max H Noori
*Assistant Examiner* — Masoud H Noori
(74) *Attorney, Agent, or Firm* — Hamre, Schumann, Mueller & Larson, P.C.

(57) ABSTRACT

Embodiments of present disclosure relates to method and device for controlled emission of radiation. Device comprises probe unit, sensor unit and switch unit. Probe unit is configured to emit radiation on surface of object. Probe unit is supported, via an elastic, to supporting structure of device. Sensor unit is placed at predefined distance from probe unit, along supporting structure, to establish contact with surface. Sensor unit comprises flexible material, mounted to supporting structure, with cavity and first force sensing unit placed in cavity of flexible material. First force sensing unit is configured to detect first force transferred from surface sensor unit. Switch unit is configured to control emission of radiation on surface, based on first force detected by first force sensing unit, upon contact of sensor unit with surface and identification of probe unit to be one of in contact with surface or at minimal distance from surface.

44 Claims, 18 Drawing Sheets

(56) References Cited

U.S. PATENT DOCUMENTS

2014/0213903 A1\* 7/2014 Seo ................. A61B 8/5207
601/3

\* cited by examiner

DEVICE AND METHOD FOR CONTROLLED EMISSION OF RADIATION

TECHNICAL FIELD

Present disclosure generally relates to devices configured to emit radiation. Particularly, but not exclusively, the present disclosure relates to device and method for controlled emission of electromagnetic radiation onto a surface of an object.

BACKGROUND

A device that is configured to emit radiation on a surface may be used for various purposes including diagnosis, determination of characteristics/properties of the surface or matter underneath the surface and so on. Emitted radiation may vary based on application of the device. An investigating device may use the emitted radiation to analyse properties associated with the surface or matter underneath it. A therapeutic device may use the emitted radiation to bring about a desired effect on the surface or matter underneath it. The investigating device may include a trans-receiver and the therapeutic device may include a transmitter. Consider the device is an optical device and the radiation emitted by the optical device is laser beams. Such lasers have applications in field of surveying, garment industry, laser nuclear fusion, communication, laser printing, spectroscopy, medical procedures and so on. The laser beams emitted from the optical device of narrow wavelength band may be referred to as monochromatic beams. Such laser beams are associated with low divergence. Due to such characteristics, the laser beams emitted during medical procedures may harm several parts of a human body especially skin and eye. Particularly, high power of the laser beams may be hazardous to an eye over considerable distances. Due to the monochromatic and the low divergence properties of the laser beams, the laser beams may directly fall on lens of the eye, thus directly affecting retina of the eye. Also, human eye is extremely sensitive to the laser beams and may be permanently damaged from direct or reflected beams. The laser beams may harm skin via photochemical or thermal burns resulting in sunburn, risk of developing skin cancer and premature aging and so on.

Existing measures for protection from an accidental exposure of the laser beams include safety goggles. The safety goggles may be worn by a user operating the optical devices. Existing measures also include costumes to cover skin to avoid contact of skin with the laser beams. However, such measures may not provision complete protection from the accidental exposures due to negligence by the user or due to unavailability or high cost of costumes or safety goggles.

Some other existing measures for the protection include, providing a maximum permissible exposure to limit the emission of the laser beams. The maximum permissible exposure is a highest power or energy density of light source that provisions negligible risk for causing damage to an exposed surface of the human body which could be skin, eye or both. In case the maximum permissible exposure is in accordance with that of skin, user's skin may not be affected by the emitted laser beams. However, the eyes are still at risk of accidental exposure.

Some of other existing systems may be configured to emit the electromagnetic radiation, based on a physical contact between probe of the optical device and surface of an object on which the electromagnetic radiation is to be emitted. Such existing systems may work with error caused in detecting contact with uneven surface. When uneven surfaces are encountered, many a times, the electromagnetic radiations may be triggering to be emitted, even if there is not proper contact of probe with the surface. This may cause Fresnel losses, erratic readings, uneven absorption and so on. Also, when the undesired emission of the electromagnetic radiation occurs, power in the optical device is consumed. Hence, proper utilization of power may not be achieved.

The information disclosed in this background of the disclosure section is only for enhancement of understanding of the general background of the invention and should not be taken as an acknowledgement or any form of suggestion that this information forms the prior art already known to a person skilled in the art.

SUMMARY OF THE DISCLOSURE

In an embodiment, the present disclosure relates to a device for controlled emission of radiation. The device comprises at least one probe unit, at least one sensor unit and at least one switch unit. The at least one probe unit is configured to emit a radiation on surface of an object. The at least one probe unit is supported, via an elastic mechanism, to a supporting structure of the device. The at least one sensor unit is placed at a predefined distance from the at least one probe unit, along the supporting structure, to establish contact with the surface. The at least one sensor unit comprises a flexible material, mounted to the supporting structure, with a cavity and a first force sensing unit placed in the cavity of the flexible material. The first force sensing unit is configured to detect first force transferred from the surface to the at least one sensor unit. The at least one switch unit is configured to control emission of the radiation on the surface, based on at least one of the first force detected by the first force sensing unit, upon contact of the at least one sensor unit with the surface and identification of the at least one probe unit to be one of in contact with the surface of the object and at a minimal distance from the surface of the object.

In an embodiment, the present disclosure relates to a method of controlled emission of radiation. The method comprises to identify at least one probe unit of a device to be one of in contact with a surface of an object and at a minimal distance from the surface of the object. The at least one probe unit is configured to emit a radiation on the surface. The at least one probe unit is supported, via an elastic mechanism, to a supporting structure of the device. The method further comprises to detect first force between at least one sensor unit and the surface, upon contact of the at least one sensor unit with the surface. The at least one sensor unit is placed at a predefined distance from the at least one sensor unit, along the supporting structure, to establish contact with the surface. The at least one sensor unit comprises a flexible material, mounted to the supporting structure, with a cavity and a first force sensing unit placed in the cavity of the flexible material. The first force sensing unit is configured to detect the first force. Upon the identification relating to the at least one probe and the detection of the first force, the method comprises to control emission of the radiation on the surface using at least one switch unit, based on at least one of the identification related to the at least one probe unit and the detection of the first force.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF DRAWINGS

The accompanying drawings, which are incorporated in and constitute a part of this disclosure, illustrate exemplary embodiments and, together with the description, serve to explain the disclosed principles. In the figures, the left-most digit(s) of a reference number identifies the figure in which the reference number first appears. The same numbers are used throughout the figures to reference like features and components. Some embodiments of system and/or methods in accordance with embodiments of the present subject matter are now described, by way of example only, and regarding the accompanying figures, in which.

DETAILED DESCRIPTION

Figure 1A:
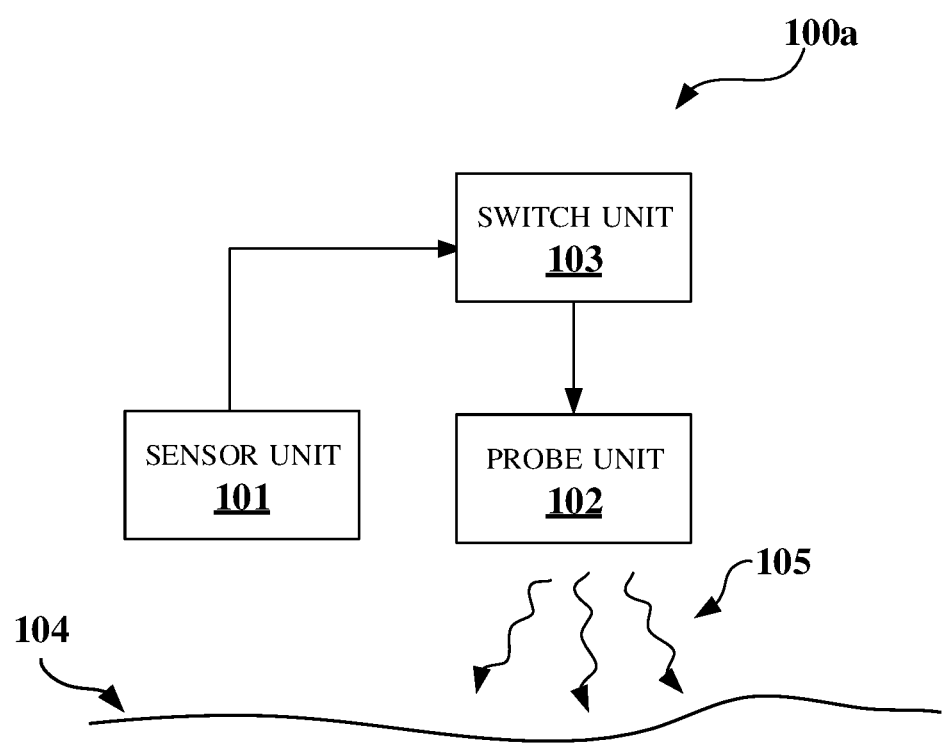
FIGS. 1a and 1b show exemplary environments of a device configured to control emission of radiation on a surface of an object, in accordance with some embodiments of the present disclosure.

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the forms disclosed, but on the contrary, the disclosure is to cover all modifications, equivalents, and alternative falling within the spirit and the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or method.

The terms "includes", "including", or any other variations thereof, are intended to cover a non-exclusive inclusion, such that a setup, device or method that includes a list of components or steps does not include only those components or steps but may include other components or steps not expressly listed or inherent to such setup or device or method. In other words, one or more elements in a system or apparatus proceeded by "includes . . . a" does not, without more constraints, preclude the existence of other elements or additional elements in the system or method.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

Present disclosure teaches a device and method for controlled emission of radiation on surface of an object. The device is configured to control the emission based on contact of the device with the surface. The device includes combination of a probe unit and a sensor unit to detect the contact and a switch unit to control the emission of the radiation. Sensors are coupled in at least one of the probe unit and the sensor unit for accurately controlling the emission of the radiation.

FIG. 1a shows an exemplary block diagram of a device 100a proposed in the present disclosure. The device 100a may be a fully automatic system configured to control emission of radiation onto a surface 104 of an object. The radiation 105 may include, but is not limited to, electromagnetic radiation, sound waves and so on. In an embodiment, the application of the device 100a may vary based on the surface 104 of the object. For example, the device 100a may be an optical device which is configured to emit laser light for treatment of skin. The object may be patient, and the surface 104 may be skin. Usually, in such applications, the surface 104 of the object may be irregular. In an embodiment, the device 100a is operated to get in contact with the surface 104 of the object. An operator of the device 100a may be configured to place the device 100a close to the surface 104 and exert force to emit the radiation 105.

As shown in FIG. 1a, the device 100a may include at least one probe unit 102, at least one sensor unit 101 and at least one switch unit 103. The at least one probe unit 102 may be configured to emit and receive or only emit the radiation 105 on the surface 104. In an embodiment, the at least one probe unit 102, for emitting the radiation 105, may include a radiation source and a driver assembly to drive the radiation source-(not shown in FIG. 1). The radiation source may generate and emit the radiation 105 onto to the surface 104. The driver assembly may be a current source which controls current to be supplied to the radiation 105. The at least one probe unit 102 may be supported in the device 100a to a supporting structure of the device 100a. The support to the supporting structure may be provided via an elastic mechanism.

The at least one sensor unit 101 in the device 100a is placed at a predefined distance from the at least one probe unit 102, along the supporting structure. Arrangement of the at least one sensor unit 101 in the device 100a establishes contact of the at least one sensor unit 101 with the surface 104. The at least one sensor unit 101 may comprise a flexible material and a first sensing unit. The flexible material may include a cavity. The at least one sensor unit 101 may be mounted to the supporting structure via the flexible material. The first force sensing unit may be placed in the cavity of the flexible material. The first force sensing unit may be configured to detect first force transferred from the surface 104 to the at least one sensor unit 101, upon contact of the at least one sensor unit 101 with the surface 104. The first force may be caused due to force exerted by the operator. The operator may be a human or a machine configured to operate the device 100a in a desired manner.

The at least one switch unit 103 may be configured to control emission of the radiation 105 on the surface 104. In an embodiment, the control may be proportional to the first force detected by the first force sensing unit. In an embodiment, the control may be based on identification of the at least one probe unit 102 to be in contact with the surface 104 of the object or at a minimal distance from the surface 104 of the object. In an embodiment, the controlling may be based on both the first force and said identification. In an embodiment, the at least one switch unit 103 may be configured to control emission of the radiation 105 by controlling supply of power to the at least one probe unit 102. In an embodiment, the at least one switch unit 103 may be configured to control emission of the radiation 105 by varying one or more properties of the radiation 105 emitted on the surface.

Figure 1B:
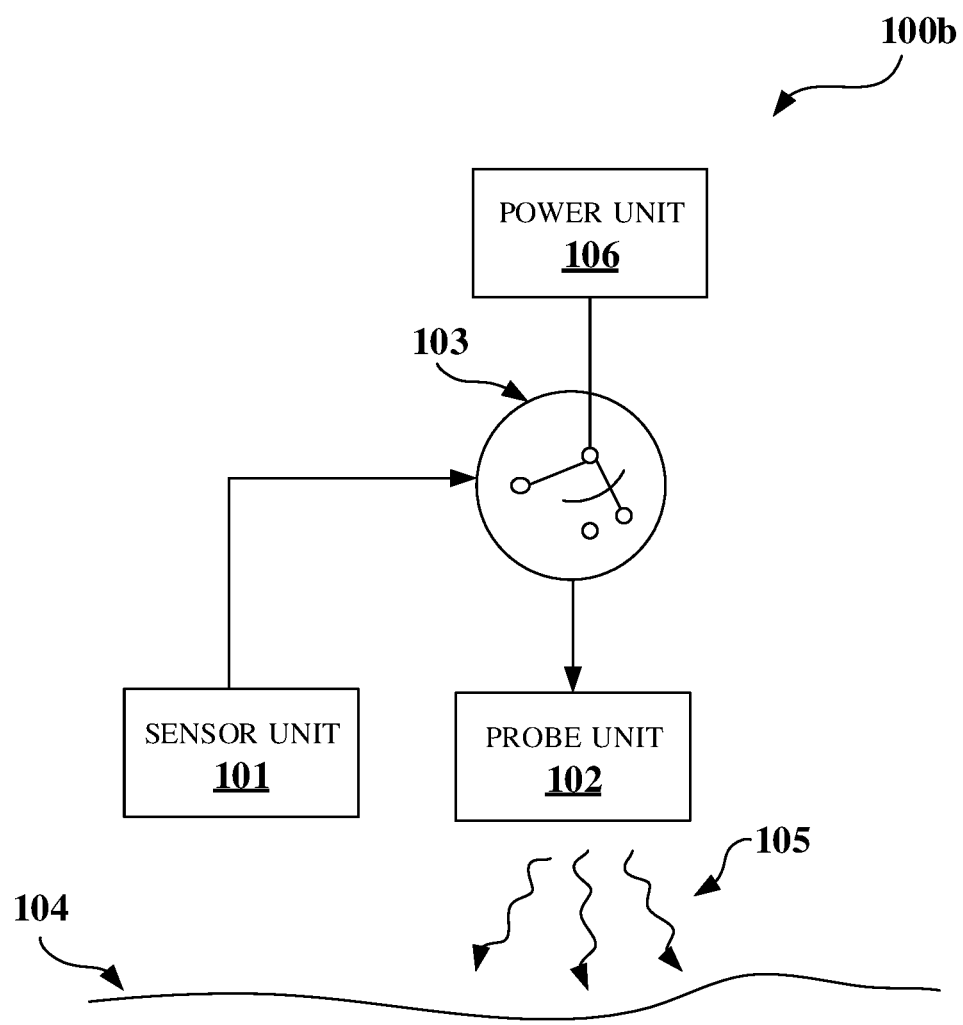

Consider the at least one switch unit 103 is configured to control supply of power to the at least one probe unit 102. An exemplary block diagram of a device 100b for controlling supply of the power to the at least one probe unit 102 is illustrated in FIG. 1b. A power unit 106 of the device 100b may be configured to supply power to the at least one probe unit 102, enabling the at least one probe unit 102 to emit the radiation 105. The at least one switch unit 103 may be configured to switch ON and OFF the supply of the power to the at least one probe unit 102, using a gate circuit. The supply from the power unit 106 may be controlled based on signal transmitted from the at least one switch unit 103. In an embodiment, the signal may be of gate values 0 or 1. The at least one sensor unit 101 may be configured to detect the first force between the surface 104 and the at least one sensor unit 101. The first force may be compared with a first threshold value. If the first force is greater than the first threshold value, then the at least one sensor unit 101 may be said to be in active state and may be configured to generate a signal. In such case, the signal may be gate value 1. The signal may be communicated with the at least one switch unit 103 and the at least one switch unit 103 may be configured to switch ON the supply of the power to the at least one probe unit 102. In an embodiment, the signal generated by the at least one sensor unit 101 may be transmitted to the at least one switch unit 103 through a conducting path. In an embodiment, the at least one switch unit 103 may receive the signal through the conducting path and close the gate circuit for transmitting power to the at least one probe unit 102. Thus, the at least one probe unit 102 may emit the electromagnetic radiation upon receiving the power from the power unit 106. Similarly, if the force is less than the first threshold value, there may be no signal generated by the at least one sensor unit 101. In an embodiment, in such condition, the at least one sensor unit 101 may be said to be in a passive state. In an embodiment, the at least one sensor unit 101 signal may be configured to generate a signal indicating gate value 0, when the at least one sensor unit 101 is in passive state. When no signal is received from the at least one sensor unit 101 or when gate value 0 is received, the at least one switch unit 103 opens the gate circuit. Thus, the power unit 106 does not supply power to the at least one probe unit 102 and the radiation 105 may not be emitted from the at least one probe unit 102. In an embodiment, the at least one switch unit 103 may be configured to control supply of power to the at least one probe unit 102 based on identification of the at least one probe unit 102 to be in contact with the surface 104 of the object or at a minimal distance from the surface 104 of the object. In such scenario, the at least one switch unit 103 may be coupled with the at least one probe unit 102 (not shown in the figure). In an embodiment, the at least one switch unit 103 may be configured to control supply of power to the at least one probe unit 102 based on both the first force and the said identification.

Consider the at least one switch unit 103 may be configured to control emission of the radiation by varying one or more properties of the radiation 105 emitted on the surface 104. The at least one switch unit 103 may be coupled with at least one of the at least one sensor unit 101 and the at least one probe unit 102. Either proportional to the first force or based on the identification or both, the one or more properties of the radiation 105 may be varying. In such scenario, the at least one switch unit 103 may be configured to adjust or vary the properties of the radiation 105. In an embodiment, the one or more properties may include, but is not limited to, intensity, frequency, wavelength, duration of emission and so on.

In an embodiment, the at least one switch unit 103 may be configured to perform both switching of supply of the power to the at least one probe unit 102 and varying the one or more properties of the radiation 105. In an embodiment, the device 100b may include more than one switch units. One of the switch units may be configured to control the supply of the power and other switch unit/units may be configured to vary the one or more properties.

Figure 2A:
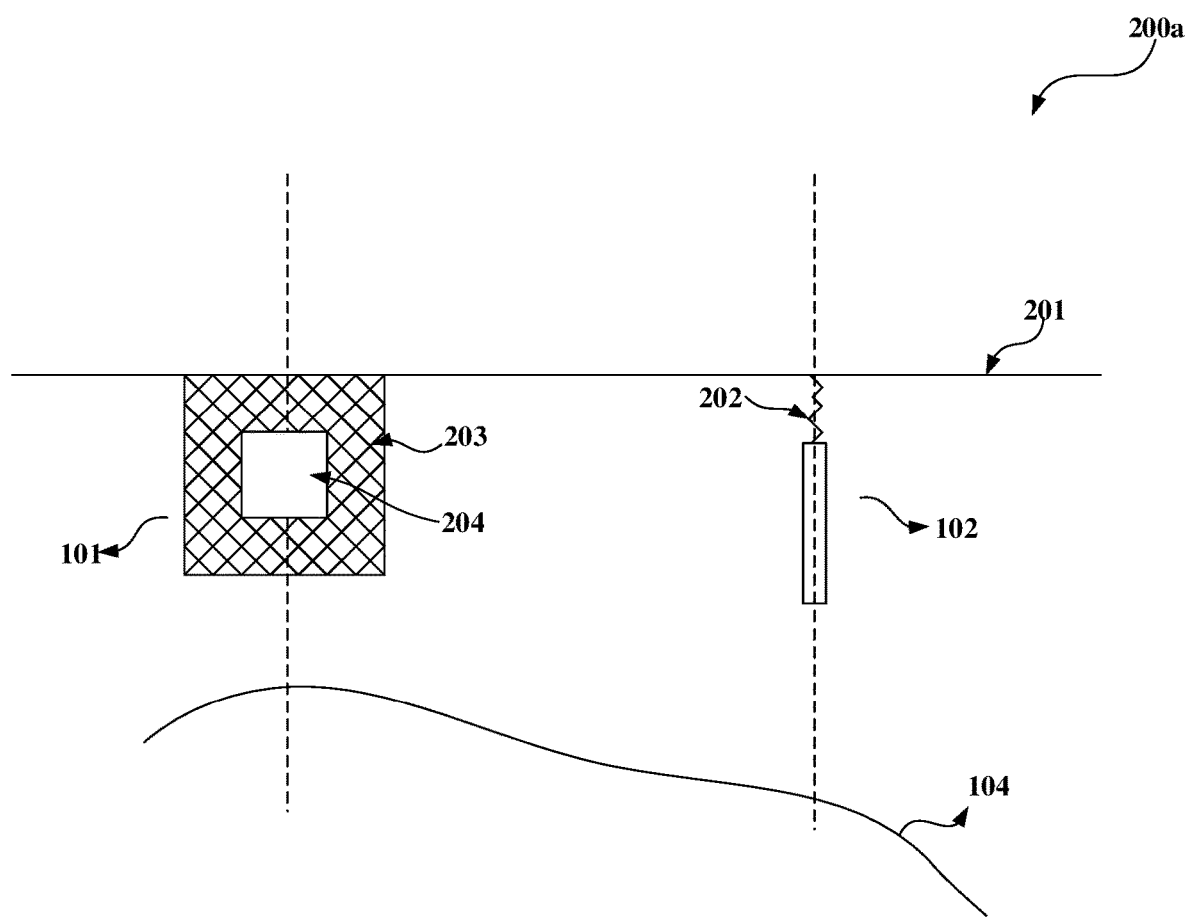
FIGS. 2a-2d show exemplary representation of device configured to control emission of radiation on a surface of an object, in accordance with some embodiments of the present disclosure.

FIG. 2a illustrates exemplary arrangement of the at least one sensor unit 101 and the at least one probe unit 102 in the device, in accordance with embodiments of the present disclosure. In the device, the at least one probe unit 102 is supported, via an elastic mechanism, to a supporting structure of the device. The at least one sensor unit 101 is placed at a predefined distance from the at least one probe unit 102, along the supporting structure, to establish contact with the surface 104. The at least one sensor unit 101 may comprise a flexible material 203 and a first sensing unit (not shown in figure). The flexible material 203 may include a cavity 204 and may be mounted to a supporting structure 201. The flexible material 203 in the at least one sensor unit 101 may be configured to compress to enable transmission of the first force between the surface 104 and the at least one sensor unit 101. In an embodiment, the flexible material may be any elastic mechanism where the elasticity is by virtue of the material properties or design of the mechanism. In an embodiment, the flexible material 203 may be a foam which is a sponge type material that can be contracted or retracted based on force applied by the operator operating the device. The flexible material 203 may get in contact with the surface 104, upon force from the operator. The flexible material 203 may be considered as fencing material covering the first force sensing unit of the at least one sensor unit 101. In an embodiment, the flexible material 203 may act as a protective material around the first force sensing unit.

Figure 2B:
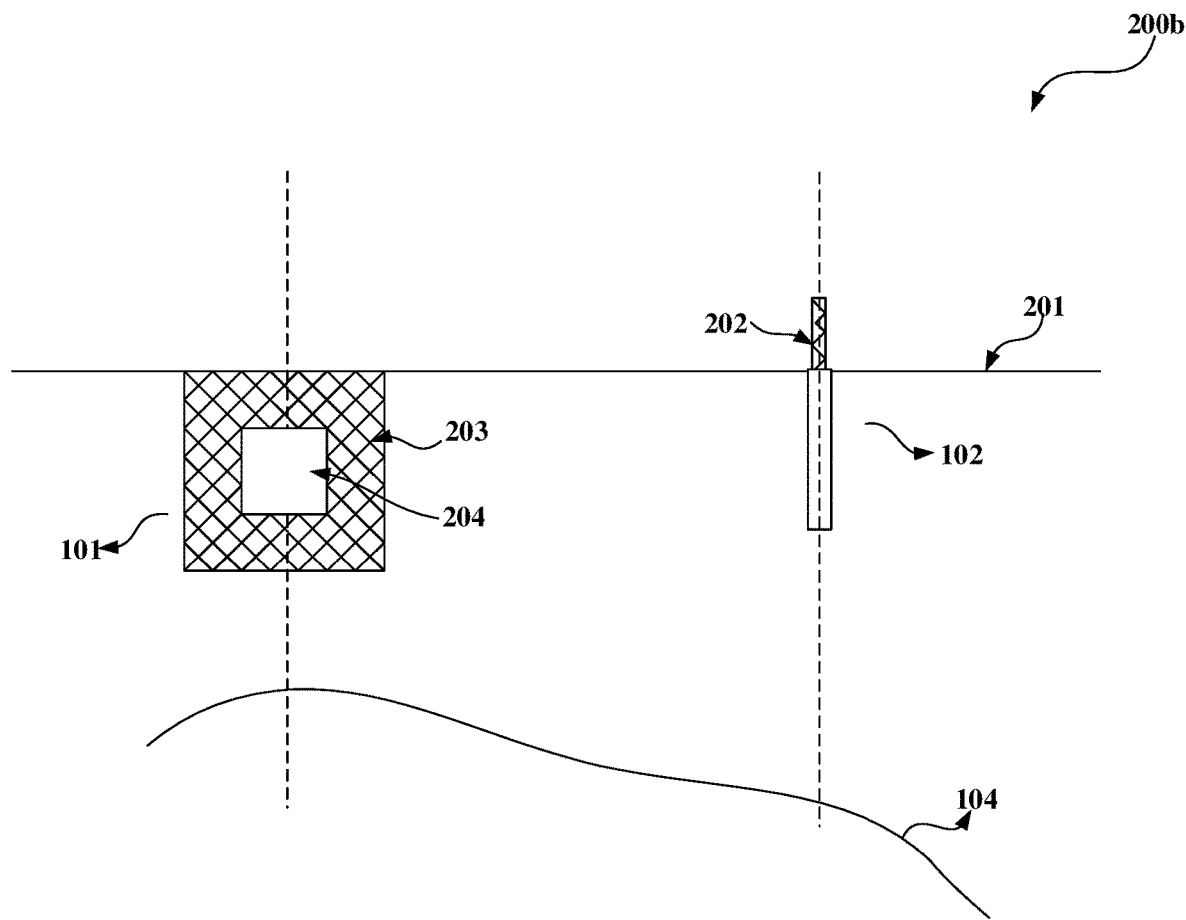
Figure 2C:
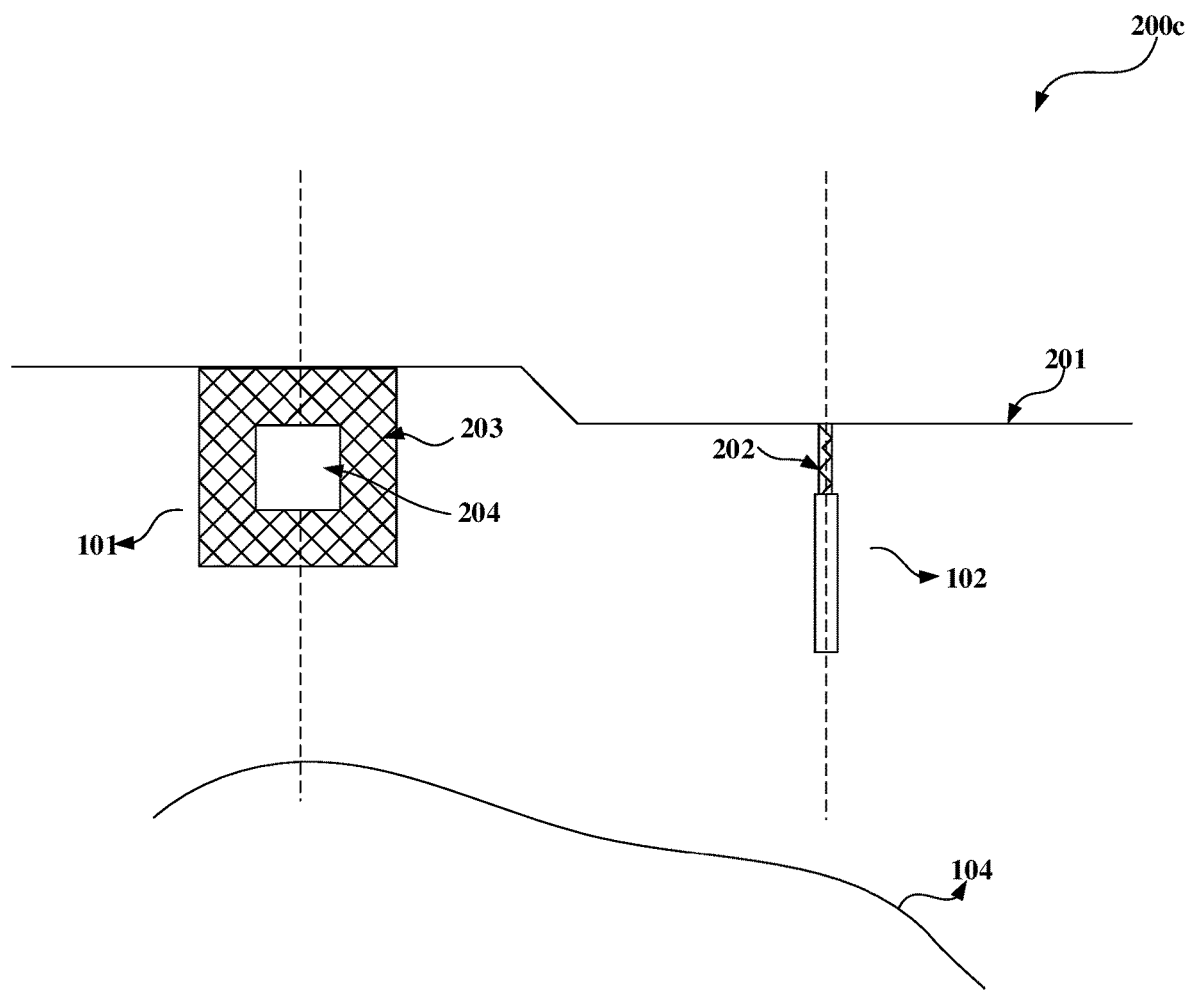
Figure 2D:
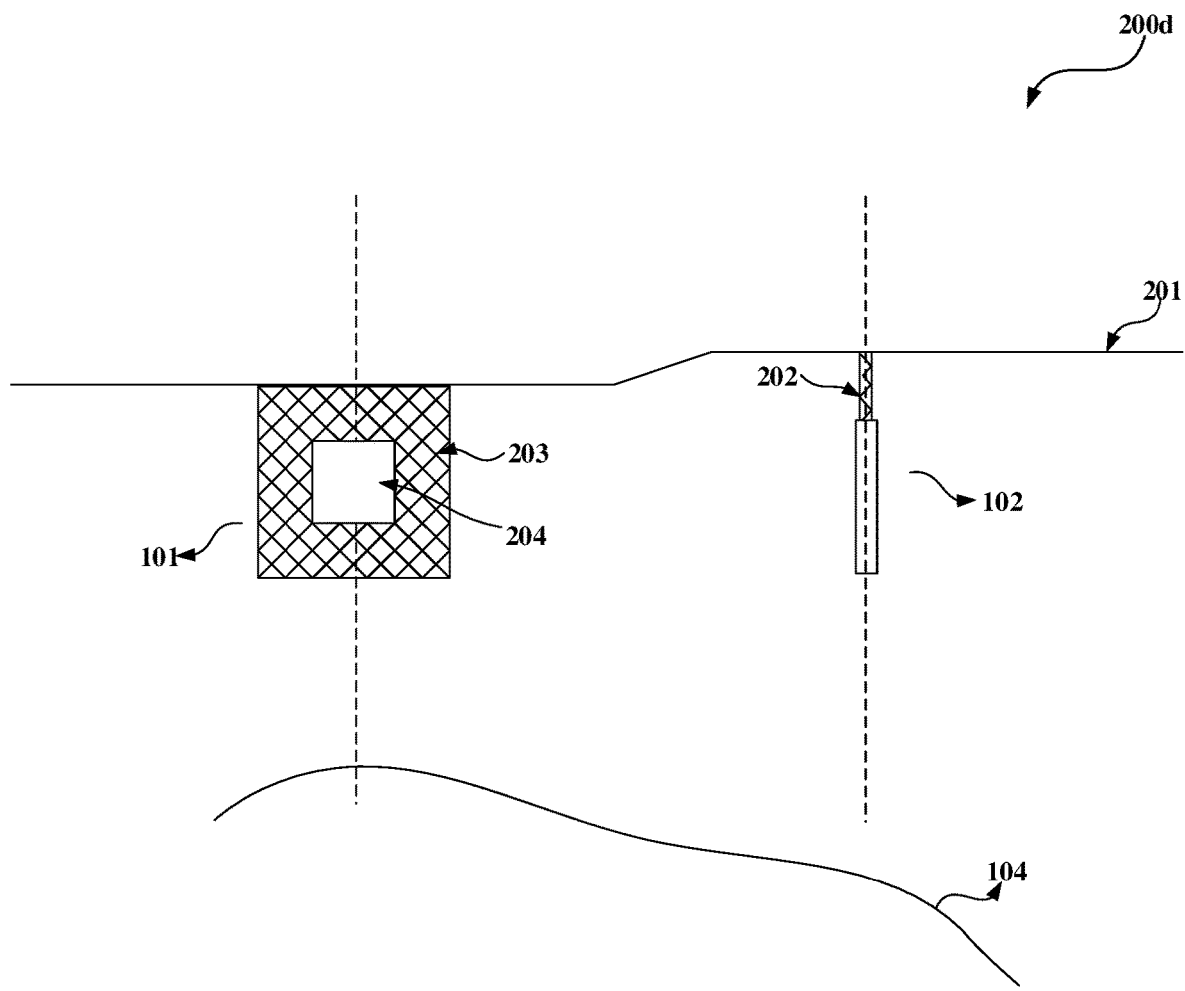

The at least one probe unit 102 may be supported, via an elastic mechanism, to the supporting structure 201 of the device. The elastic mechanism may be achieved using any elastic material/elastic element 202. In an embodiment, as shown in the figure, the elastic mechanism may be achieved using a spring. In an embodiment, the spring may be replaced with any component or mechanism with properties of compressibility. The at least one sensor unit 101 and the at least one probe unit 102 are placed at a predefined distance from each other. In an embodiment, the portion of the supporting structure 201 supporting the at least one probe unit 102 is of different plane with respect to portion of the supporting structure 201 mounting the at least one sensor unit 101. Some of exemplary arrangements of the at least one sensor unit 101 and the at least one probe unit 102 is shown in FIGS. 2b-2d.

In an embodiment, the first force sensing unit of the at least one sensor unit 101 may be configured to detect the first force transferred from the surface 104 to the at least one sensor unit 101. In an embodiment, the first force between the surface 104 and the at least one sensor unit 101 may be in axial direction, transverse direction, torsional direction or combination thereof.

Figure 3A:
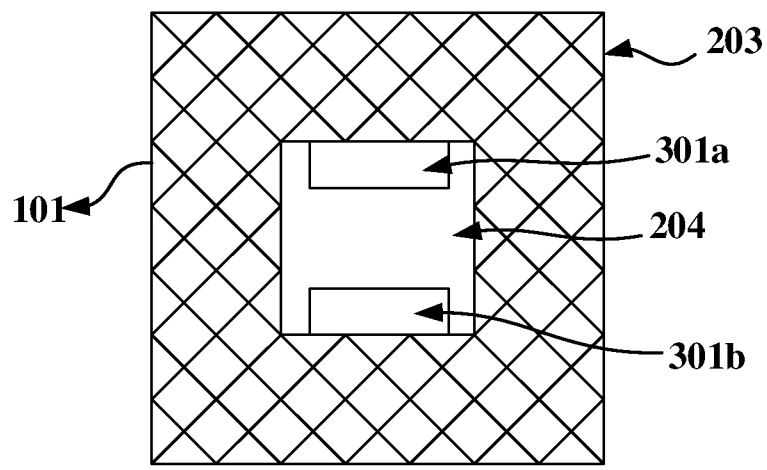
FIGS. 3a-3e show exemplary representation of sensor unit in a device configured to control emission of radiation on a surface of an object, in accordance with some embodiments of the present disclosure.

In an embodiment, the first force sensing unit may include two plates placed on opposite sides of the cavity 204. An exemplary arrangement of the at least one sensor unit 101 with two plates 301a and 301b is shown in FIG. 3a. When a force is exerted by the operator, the flexible material 203 may be configured to compress and distance between the two plates 301a and 301b may decrease. Hence, the first force is transferred from the surface 104 towards the supporting structure 201. In an embodiment, the distance between the two plates 301a and 301b may be monitored. In an embodiment, the at least one switch unit 103 may be configured to control emission of the radiation 105 on the surface 104 when the distance between the two plates 301a and 301b is zero. In one exemplary embodiment, the two plates 301a and 301b may be two contact plates of a switch. When the contact plates are in contact with each other, the at least one switch unit 103 may be enabled to control emission of the radiation 105.

Figure 3B:
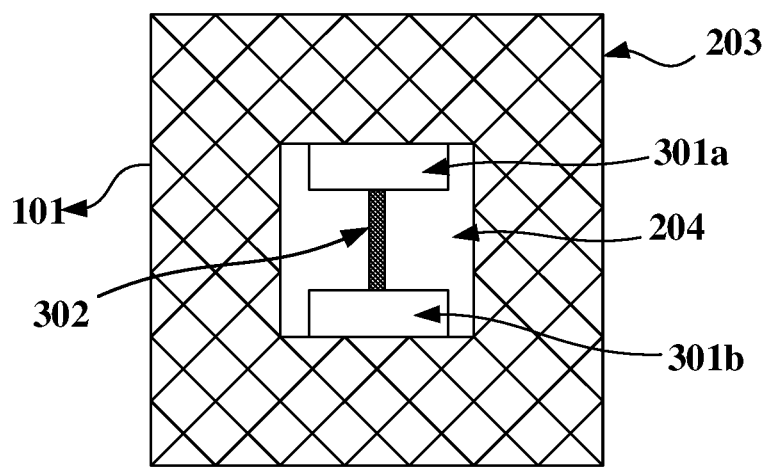

In an embodiment, the first force sensing unit may include a flex sensor along with the two plates 301a and 301b on opposite sides of the cavity 204. An exemplary arrangement of the at least one sensor unit 101 with the two plates 301a and 301b and a flex sensor 302 is shown in FIG. 3b. When a force is exerted by the operator, the flexible material 203 may be configured to compress and distance between the two plates 301a and 301b may decrease. Decrease in distance between the two plates 301a and 301b may cause flex or bend in the flex sensor 302. The flex sensor 302 may be configured to determine flex parameter associated with the flex or the bend. The flex parameter is directly proportional to the first force.

Figure 3C:
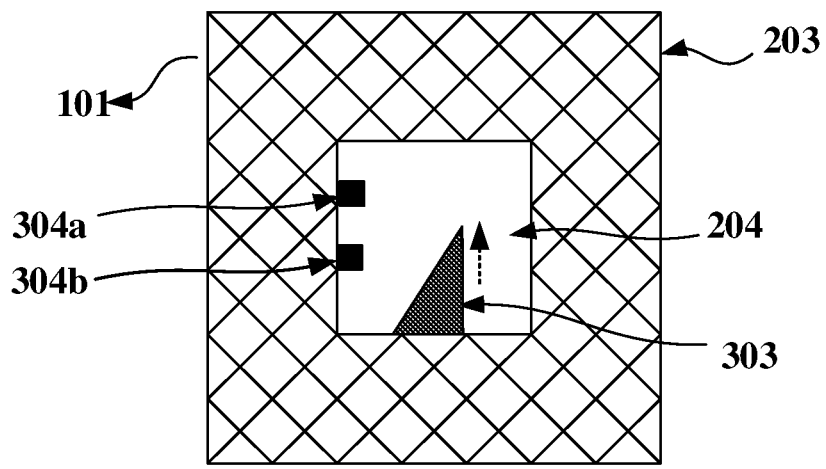

In an embodiment, the first force sensing unit may include a block along with at least one of Infrared (IR) sensor and sound sensor. An exemplary arrangement of the at least one sensor unit 101 with a block 303 and at least one of the IR sensor and the sound sensor is shown in FIG. 3c. The block 303 may be configured to displace when the first force is transferred from the surface 104. The at least one of the IR sensor and the sound sensor may be configured to determine displacement of the block 303 inside the cavity 204. Each of the IR sensor or the sound sensor may include a transmitter 304b and a receiver 304a. The transmitter 304b may be configured to emit IR rays or sound waves. The receiver 304a may receive the reflected IR rays or the reflected sound waves. Using the reflected IR rays or the reflected sound waves, the displacement of the block 303 may be determined. The displacement is directly proportional to the first force. In an embodiment, the block 303 may be replaced by any moving part inside the device, whose displacement is proportional to the first force.

Figure 3D:
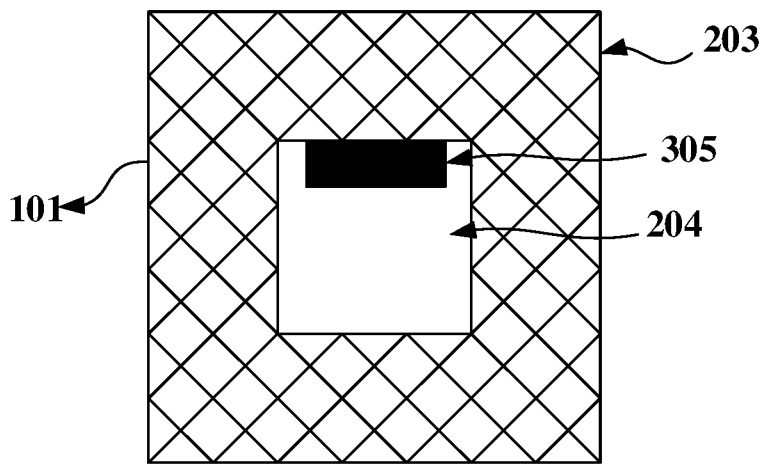

In an embodiment, the first force sensing unit may include a force sensor. An exemplary arrangement of the at least one sensor unit with the force sensor 305 is shown in FIG. 3d. In an embodiment, the force sensor may be at least one of stress sensor, touch sensor and strain gauge sensor, pressure sensor and so on, which is configured to determine force between the surface 104 and the at least one sensor unit. In an embodiment, the force may be in form of pressure, stress, touch and strain and so on, which is caused due to the first force transferred from the surface 104. The force is directly proportional to the first force.

Figure 3E:
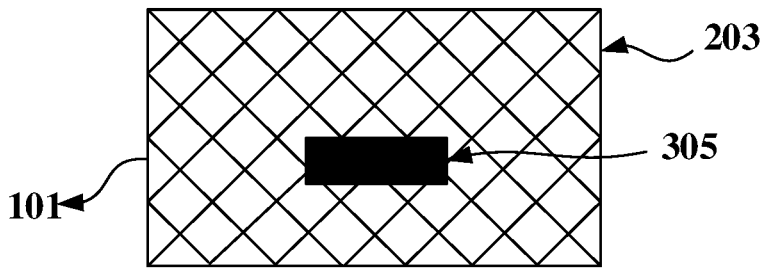

In an embodiment, the first force sensing unit may be embedded inside the at least one sensor unit 101, covering the cavity. An exemplary representation of such arrangement is illustrated in FIG. 3e. In the exemplary representation, the force sensor 305 is embedded inside the at least one sensor unit 101. The force exerted on the flexible material may be detected by the force sensor 305. The determined force is directly proportional to the first force.

In an embodiment, the first force sensing unit may implement any sensor which may output a parameter proportional to the first force. In an embodiment, the first force sensing unit may implement combination of sensors. In an embodiment, the device may include a processing module which is configured to receive at least one of the distance between the two plates 301a and 301b, the flex parameter, the displacement of the block 303, the force, to determine the first force at the at least one sensor unit 101.

Figure 4:
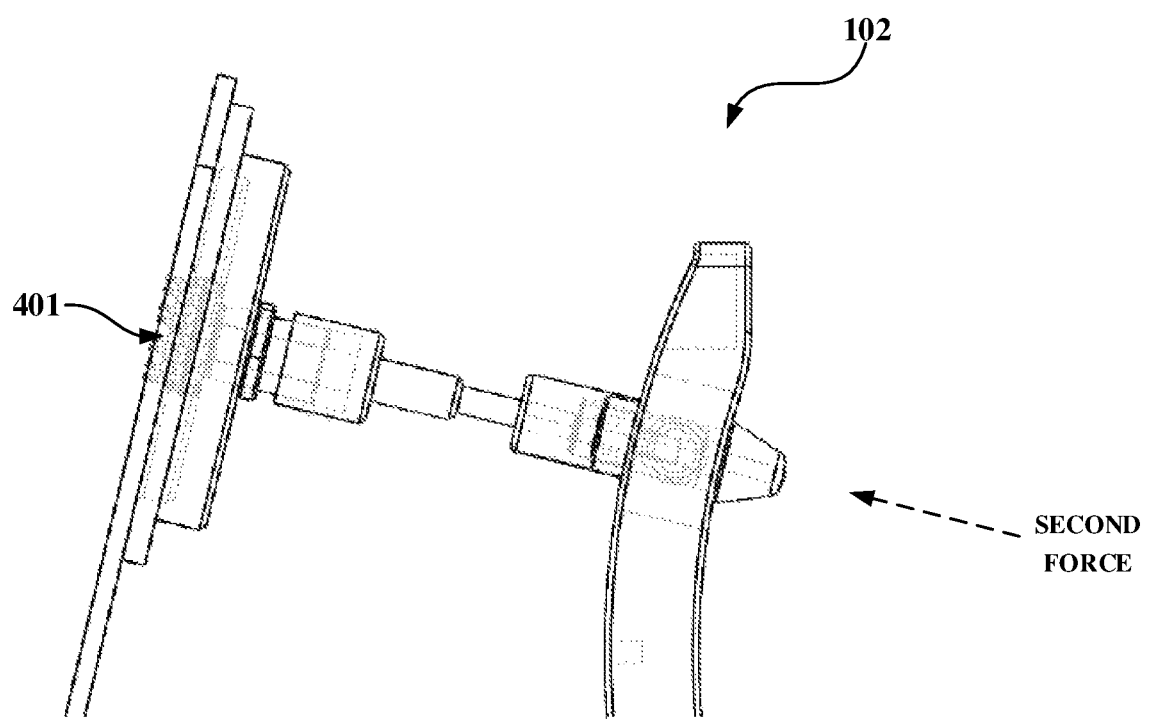
FIGS. 4, 5a and 5b show exemplary representation of probe unit in a device configured to control emission of radiation on a surface of an object, in accordance with some embodiments of the present disclosure.

In an embodiment, the at least one probe unit 102 may include a second force sensing unit. The second force sensing unit may be coupled with the at least one probe unit 102. In an embodiment, the second force sensing unit may be configured to detect a second force transferred between the surface 104 and the at least one probe unit 102. In an embodiment, the second force sensing unit may be a force sensor. In an embodiment, the force sensor may be at least one of stress sensor, touch sensor, pressure sensor and strain gauge sensor and so on, which is configured to determine the force between the surface 104 and the at least one probe unit. In an embodiment, the force may be in form of pressure, stress, touch and strain and so on. The force is directly proportional to the second force. An exemplary arrangement of the at least one probe unit 102 with the force sensor 401 is shown in FIG. 4.

Figure 5A:
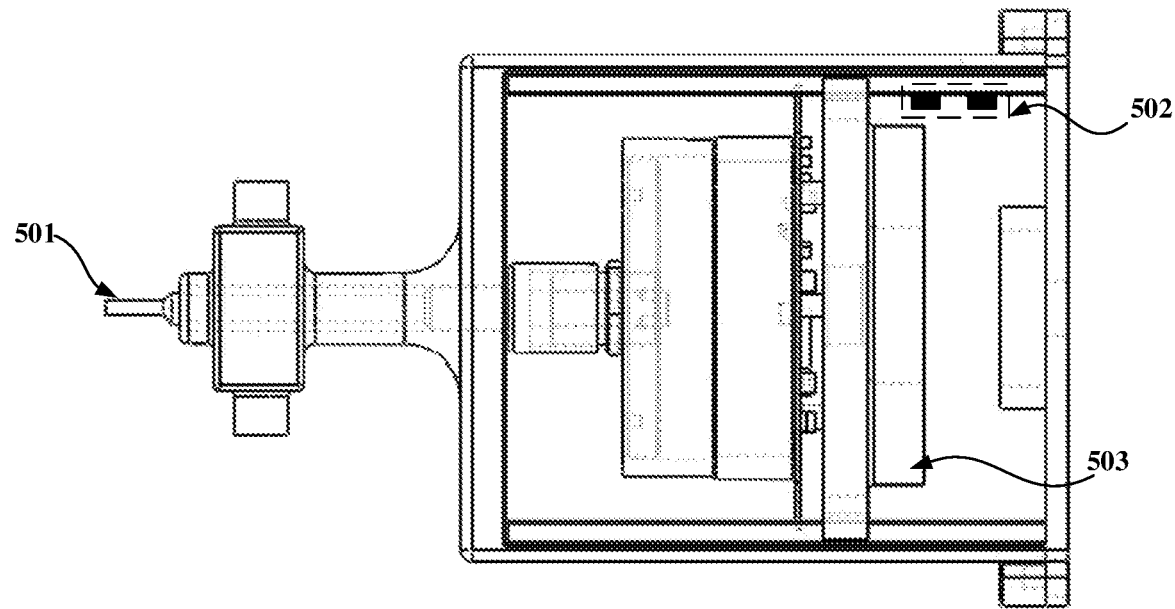
Figure 5B:
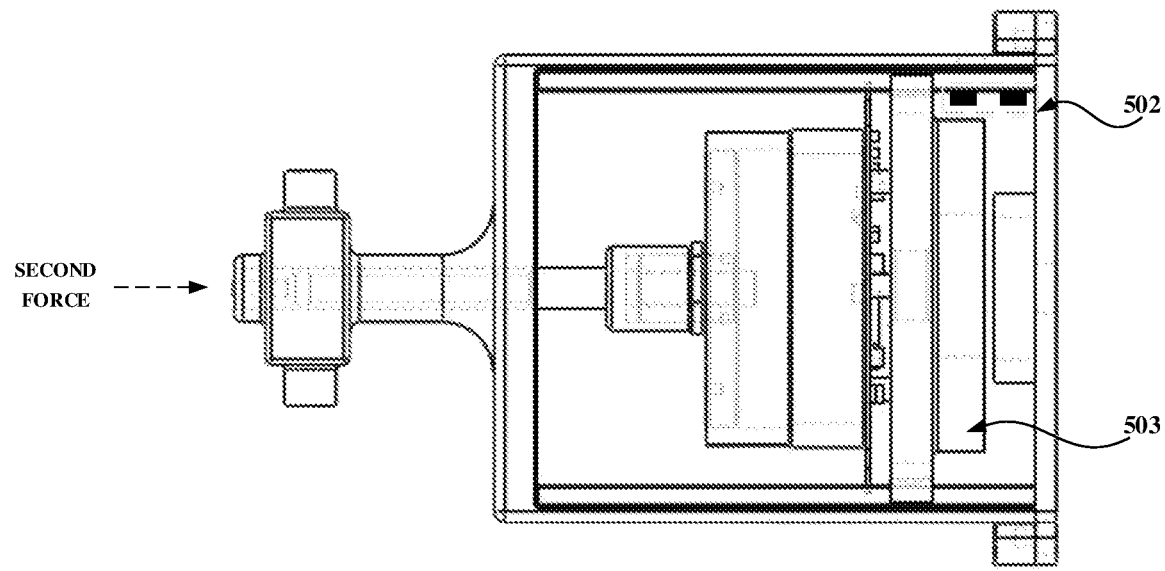

In an embodiment, the second force sensing unit may be at least one of IR sensor and sound sensor 502, coupled with a movable cable 501 in the at least one probe unit 102, as shown in FIG. 5a. The at least one of the IR sensor and the sound sensor 502 may be configured to determine displacement of the movable cable 501 caused due to the second force transferred from the surface. As shown in FIG. 5b, the displacement may be determined by transmitting IR rays or sound waves. A movable plate 503 which is part of the movable cable 501 may aid in reflection of the IR rays or the sound waves, when the displacement of the movable cable 501 has occurred. The reflected IR rays or the reflected sound waves are used to determine the displacement. The displacement is directly proportional to the second force.

In an embodiment, the second force sensing unit may implement any sensor which may output a parameter proportional to the second force. In an embodiment, the second force sensing unit may implement combination of sensors. In an embodiment, the processing module of the device may be configured to receive at least one of the displacement of the movable cable 501, the force to determine the second force at the at least one probe unit 102. In an embodiment, the at least one switch unit 103 is configured to control emission of the radiation 105 on the surface 104 by detecting the second force to be greater than a second threshold value.

In an embodiment, the processing unit of the device may be configured to adjust at least one of the first threshold value and the second threshold value. In an embodiment, at least one of the first threshold value and the second threshold value may be adjusted either manually or automatically, based on one or more factors associated with the device. In an embodiment, the one or more factors may depend on geography/environment of operation of the device. In an embodiment, the one or more factors may depend on the operator of the device or the object on which the device is operated. One or more other factor, known to a person skilled in the art may be included, for adjusting at least one of the first threshold value and the second threshold value.

In an embodiment, the identification of the at least one probe unit 102 to be at the minimal distance is performed when radius of curvature of the surface 104 is known in advance. The displacement in the sensor or the first force is proportional to the minimal distance of the at least one probe unit to the surface. In such scenario, the at least one switch unit 103 may be configured to control emission of the radiation 105 on the surface 104 upon identification of the at least one probe unit 102 to be at the minimal distance. In an embodiment, the minimal distance associated with the at least one probe unit 102 and the surface 104 of the object may be derived based on radius of curvature of the surface 104

Figure 6A:
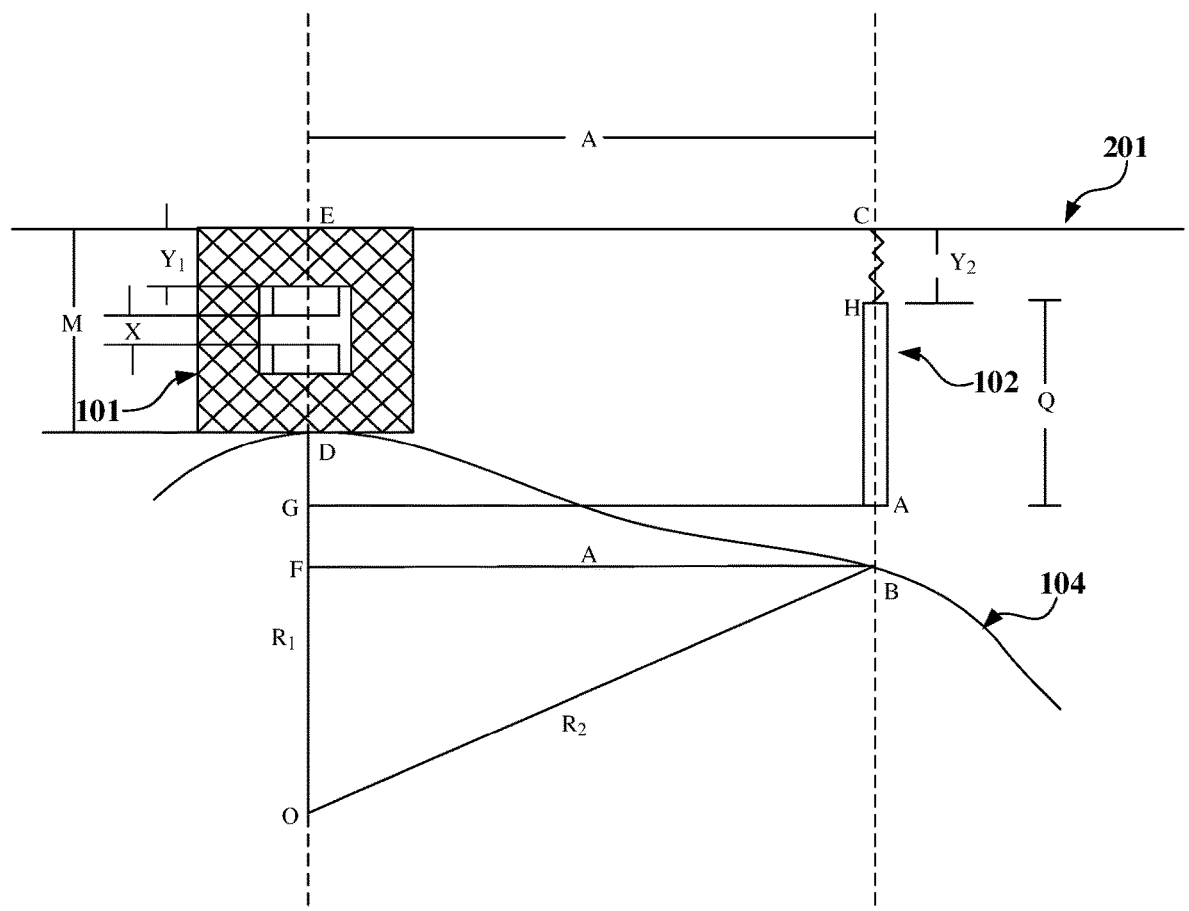
FIGS. 6a-6f illustrate exemplary embodiments of a device with single sensor unit and single probe unit, in accordance with some embodiments of present disclosure.

FIG. 6a illustrates an exemplary representation of device for computing the minimal distance between the at least one probe unit 102 and the surface 104, in accordance with embodiments of the present disclosure. Computation of distance between the at least one probe unit 102 and the surface 104 may be necessary to determine value of length of the flexible material and length of the elastic element. Consider "y1" as the length of the flexible material at any given time and "y2" as the length of the elastic element 202 at any given time. Maximum distance between point "A" and point "B" may be referred to as $(AtoB)_{max}$. Similarly, minimum distance between point "A" and point "B" may be referred to as $(AtoB)_{min}$. Consider distance between the two plates of the first sensing unit as "x". Length of the at least one probe unit 102 may be indicated as "q" which is equal to distance between end points of the at least one probe unit 102 including point A" and point "H". The distance between end points of the at least one sensor unit 101 including point "E" and point "D" may be indicated as "m". Distance between axial lines of the at least one sensor unit 101 and the at least one probe unit 102 may be indicated as "a". The distance between the axial lines "a" includes point "E" and point "C". Distance between point "A" and point "G" (hereafter referred as "AG") is equal to distance between point "E" and point "C" (hereafter referred as "EC"). Consider, the distance "EC" and "AG" is equal to value "a". Consider the surface is irregular with radius of curvature "r1" at the point "D" and radius of curvature "r2" at the point "B". Let point "O" be a centre point of the axial line of the at least one sensor unit 101. Maximum permissible compression of the flexible material allowed may be referred to as "$y1_{max}$". Similarly, maximum permissible compression of the elastic element allowed at point "A" may be referred to as "$y2_{max}$".

Consider the value of "x" is known and also $(A to B)_{max}$ and $(A to B)_{min}$ is predetermined. Based on "x", $(A to B)_{max}$ and $(A to B)_{min}$, "$y1_{max}$" and "$y2_{max}$" may be calculated using equations 1 and 2, respectively.

$$y1_{max} = (A\ to\ B)_{max} - x \tag{1}$$

$$y2_{max} = x - (A\ to\ B)_{min} \tag{2}$$

In another aspect, consider values "$y1_{max}$", "$y2_{max}$" and the distance between the point "A" to the point "B" referred to as "p" is known. Based on the value "p", the value of "x" may be determined using equation 3, given below.

$$\text{Value of "}x\text{" lies between } [(p - y1_{max}), (p + y2_{max})] \tag{3}$$

The equation 3 may determine possible value of "x" whose value may lie between $[(p - y1_{max}), (p + y2_{max})]$.

Also, from FIG. 6a, it may be said that, at any moment, distance between the point "E" and the point "D" may be equal to "m". The distance between point "E" and point "C" is same as the distance between point "F" and point "B" and may have the value "a". The distance between point "A" and point "H" may be referred to as "q".

Therefore, $EC = FB = a$ $AH = q$ $OD = r1$ and $OB = r2$.

Considering triangle OBF, from Pythagoras theorem that, it may be derived that:

$(OB)^2 = (OF)^2 + (FB)^2$ $(OF)^2 = (OB)^2 - (FB)^2$ $(OF)^2 = (r2)^2 - (a)^2$ $(OF) = ((r2)^2 - (a)^2))^{1/2}$

Also, it can be said that $OD = OF + FD$ $FD = OD - OF$ $FD = r1 - ((r2)^2 - (a)^2)^{1/2}$ Also, from FIG. 6a, the distance between the point "F" and the point "G" can be substituted as, $FG = FD - DG$ $FG = FD - DG + ED - ED$ $FG = FD - (DG + ED) + ED$ $FG = FD - GE + ED$ $AB = FD - AC + ED$ $AB = FD - (AH + HC) + ED$ $AB = r1 - ((r2)^2 - (a)^2)^{1/2} - (q + y2) + m$ $AB = r1 + m - ((r2)^2 - (a)^2)^{1/2} - q - y2$ $$AB = r1 + m - ((r2)^2 - (a)^2)^{1/2} - q - y2 \tag{4}$$

Considering distance between two plates and the flexible material negligible, $$m = y1 + x$$

so, $$AB = r1 + y1 + x + ((r2)^2 - (a)^2)^{1/2} - q - y2 \quad (5)$$

Thus, the distance between the point "A" and the point "B" can be calculated by using equation 4. When the distance between point "A" and point "B" is zero, it may be said that the at least one probe unit 102 is in contact with the surface 104.

In an embodiment, the surface 104 may have irregularities and it may not be possible for both the at least one sensor unit 101 and the at least one probe unit 102 to be in contact with the surface 104.

Due to the irregularities, with the proposed device, one or more possibilities of the contact of each of the at least one sensor unit 101 and the at least one probe unit 102 with the surface 104 is illustrated. The one or more possibilities may include, but limited to, following scenarios.

Scenario 1: Initially, the at least one sensor unit 101 touches the surface 104. Upon the force applied by the operator, the two plates of the at least one sensor unit 101 coincides first and distance between point "A" and point "B" is equal to value x.

Scenario 2: The at least one sensor unit 101 first touches the surface 104. Upon the force applied by the operator, the two plates of the at least one sensor unit 101 coincides first and distance between point "A" and point "B" is more than x.

Scenario 3: The at least one probe unit 102 first touches the surface 104. In this case, the at least one probe unit 102 touches the surface 104 first and distance between the point "A" to point "B" may be zero and the value of x to be 0 needs to be ensured for the emission of the radiation 105.

FIG. 6a illustrates first step of scenario 1 and scenario 2. Initially, consider the flexible material of the at least one sensor unit 101 may be in contact with the surface 104. But the two plates may not be touching each other. The at least one probe unit 102 may also not be in contact with the surface 104. The at least one probe unit 102 is connected to the supporting structure 201 using the elastic element or elastic mechanism whose length is "y2". In this case, the value of "x" and distance between point "A" and point "B" is not zero. Also, the first force and the second force may be determined to be minimal or zero. Thus, the radiation may not be emitted.

Figure 6B:
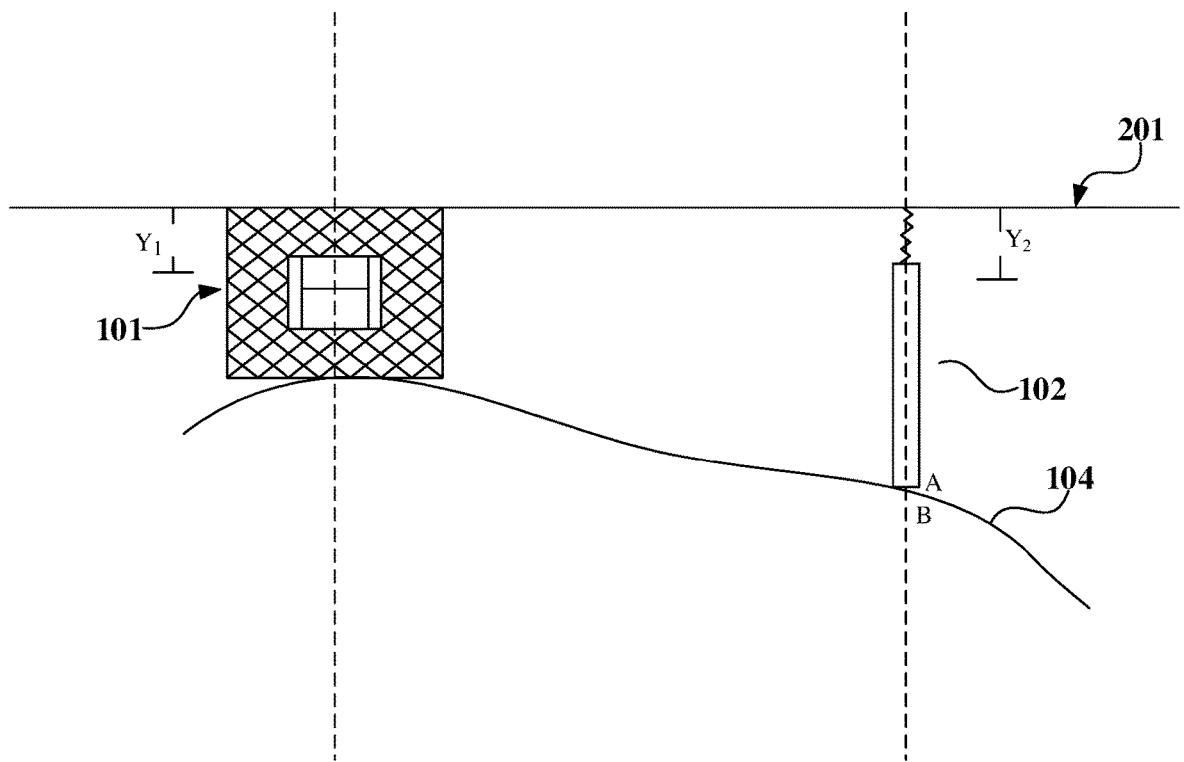

FIG. 6b illustrates exemplary representation of the device with the at least one sensor unit 101 and the at least one probe unit 102 to control emission of the radiation, in accordance with embodiments of the present disclosure. FIG. 6b also illustrates second step of scenario 1. Following the first step of scenario 1, the second step is, in-order to emit the radiation, the at least one sensor unit 101 is pushed on the surface 104 by an external force applied from the operator. By pushing the at least one sensor unit 101 on the surface 104, the point "A" comes in contact with the point "B" and also at the same time value of "x" becomes zero (i.e., upper plate coincides with lower plate in the first force sensing unit). Based on the force applied, the flexible material is compressed, and the length of the flexible material becomes less than "$y1_{max}$" value. It may be determined that at least one of the first force or the second force is determined to be greater than the first threshold value or the second threshold value, respectively. Thus, the at least one probe unit 102 emits the radiation. In this case, the value of "y1" and "y2" is not equal to zero.

Figure 6C:
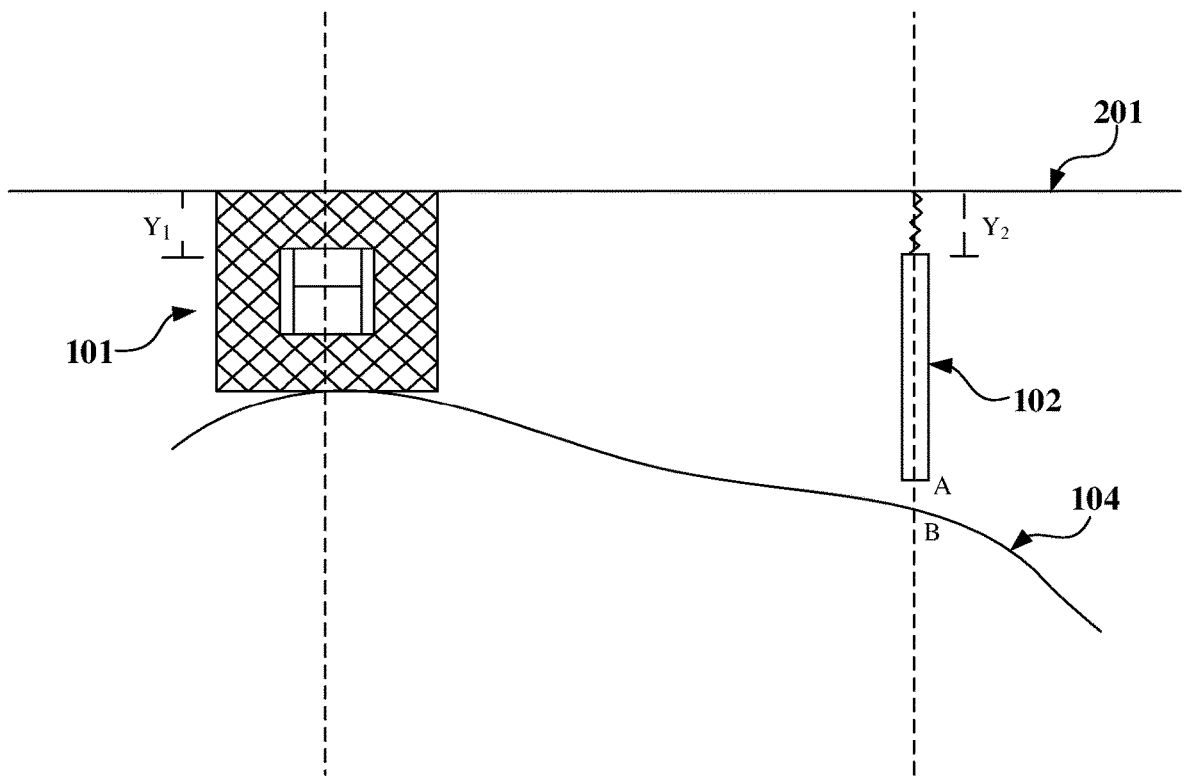

FIG. 6c illustrates second step of scenario 2. Following the first step of scenario 2, the second step may be, in-order to emit the radiation, the at least one sensor unit 101 is pushed on the surface by applying a force externally from the operator. The force applied by the operator may compress the flexible material whose length becomes less than "$y1_{max}$". The compression of the flexible material enables contact of the two plates. But, the point "A" may not coincide with the point "B". In this case, the radiation may be emitted because there is no contact between the at least one probe unit 102 and the surface 104, but, value of distance between point "A" and a point "B" is equal to the minimal distance. In an embodiment, a proximity sensor may be coupled with the at least one probe unit 102 to determine the distance between the at least one probe unit 102 and the surface 104. Output of proximity sensor may be compared with value of minimal distance to control the emission of radiation.

In this case the distance between point "A" and a point "B" is limited by controlling and designing the length "y1" and "y2". The same is depicted in equation 5. In majority of cases of devices, the distance between "A" and a point "B" would be required to be zero. Hence, the length of the flexible material ("y1") and the length of the elastic material ("y2") is selected in order to achieve distance between point "A" and point "B" equals to zero before the two plates coincide (i.e., x=0). [refer equations 1 and 2].

Figure 6D:
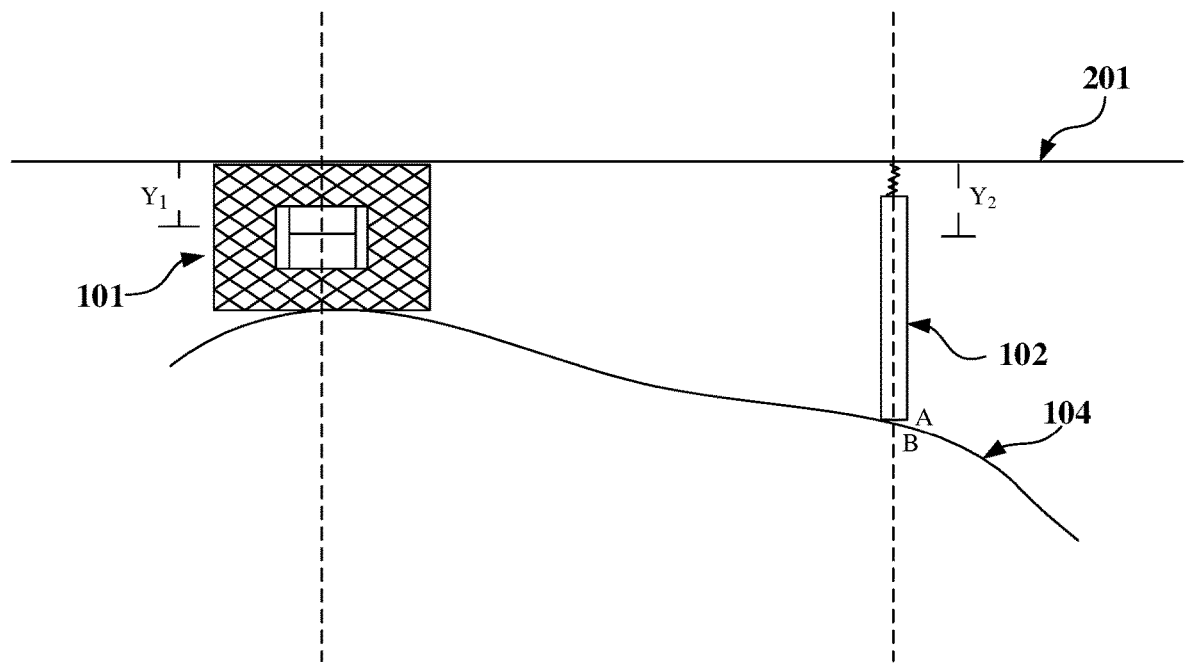

FIG. 6d illustrates third step of scenario 2. Further, the flexible material may be compressed to its maximum value referred to as "$y1_{max}$". Upon the maximum compression of the flexible material, the point "A" coincides with the point "B". As a result, the at least one probe unit 102 comes in contact with the surface 104. Also the elastic element is compressed due to the contact of the at least one probe unit 102 with the surface 104. Thus, the length of the elastic element may be less than the "y2max". Upon proper contact of the at least one probe unit 102 and the at least one sensor unit 101 with the surface 104, and upon determining that at least one of the first force or the second force to be greater than the first threshold value or the second threshold value, respectively, the radiation may be emitted. Hence, the radiation is emitted only when the distance between point "A" and point "B" is within the desired limit.

Figure 6E:
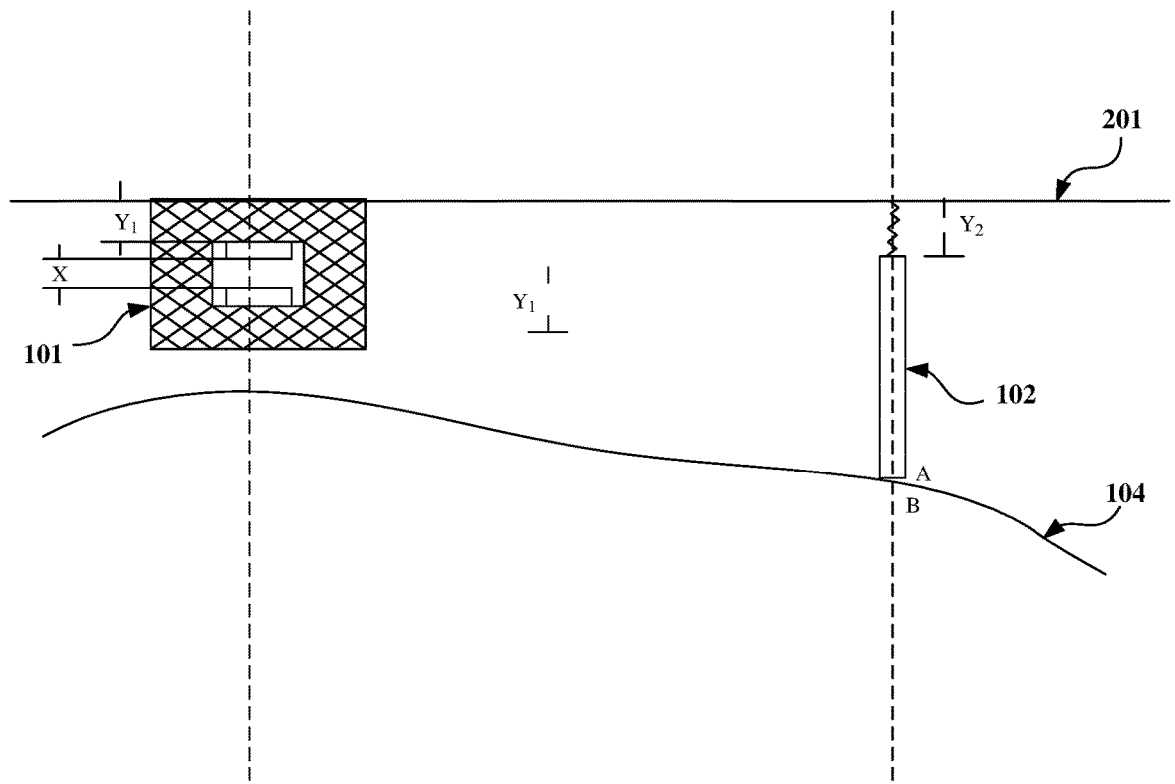

FIG. 6e illustrates first step of scenario 3. In this step, it may be possible that the at least one probe unit 102 may come in contact with the surface 104. The distance between the point "A" and the point "B" is zero. But, at the same time the at least one sensor unit 101 may not be in contact with the surface. The distance between the at least one sensor unit 101 and the surface may lie between values zero and "y2". Also, the value of "x" may not be equal to zero.

Figure 6F:
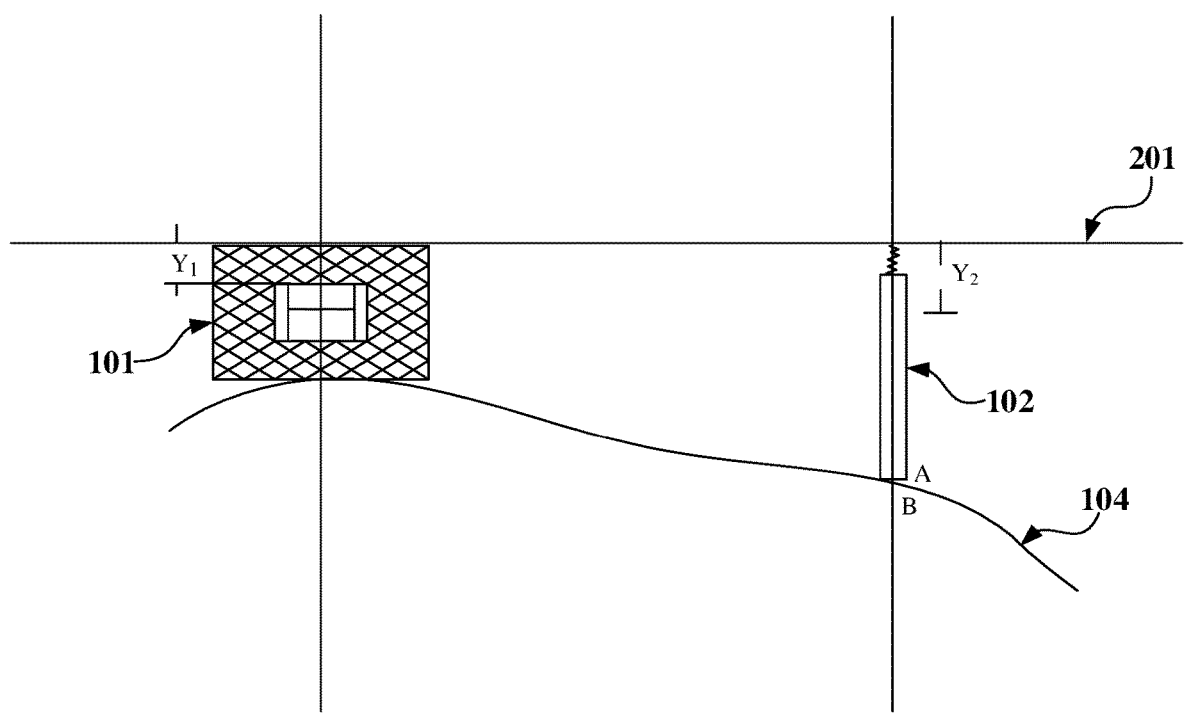

FIG. 6f illustrates second step of scenario 3. Further, the elastic element is retracted to its maximum value referred to as y2max at point "A". The elastic element is retracted due to the force applied by the operator. The maximum retraction at the point "A" ensures the contact of the two plates. Also, at the same time the flexible material of the at least one sensor unit 101 touches the surface 104. Upon contact of the at least one probe unit 102 and the at least one sensor unit 101 with the surface 104 and upon determining that at least one of the first force or the second force to be greater than the first threshold value or the second threshold value, respectively, the radiation may be emitted.

Figure 7A:
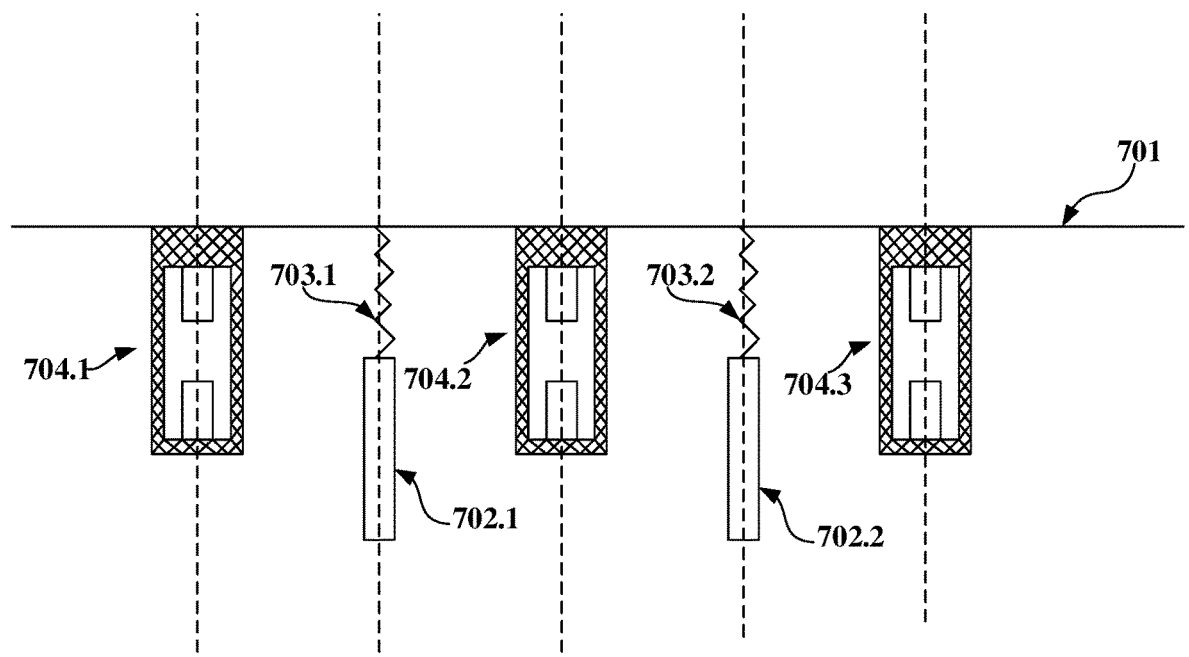
FIGS. 7a-7g illustrate exemplary embodiments of a device with plurality of sensor units and plurality of probe units, in accordance with some embodiments of present disclosure It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether such computer or processor is explicitly shown.

FIG. 7a illustrates exemplary representation of the device with plurality of sensor units 704.1, 704.2 and 704.3 (hereafter referred to as plurality of sensor units 704) and plurality of probe units 702.1 and 702.2 (hereafter referred to as plurality of probe units 702). The plurality of sensor units 704 and the plurality of probe units 702 are attached to a supporting structure 701, as shown in the figure. Each of the one or more sensor units 704 may include a first force sensing unit accommodated in cavity of respective flexible material. First force associated with each of the plurality of sensor units 704, may be determined by corresponding first force sensing unit. Each of the plurality of probe units 702 may be coupled with second force sensing unit. Second force associated with each of the plurality of probe units 702, may be determined by corresponding second force sensing unit.

Figure 7B:
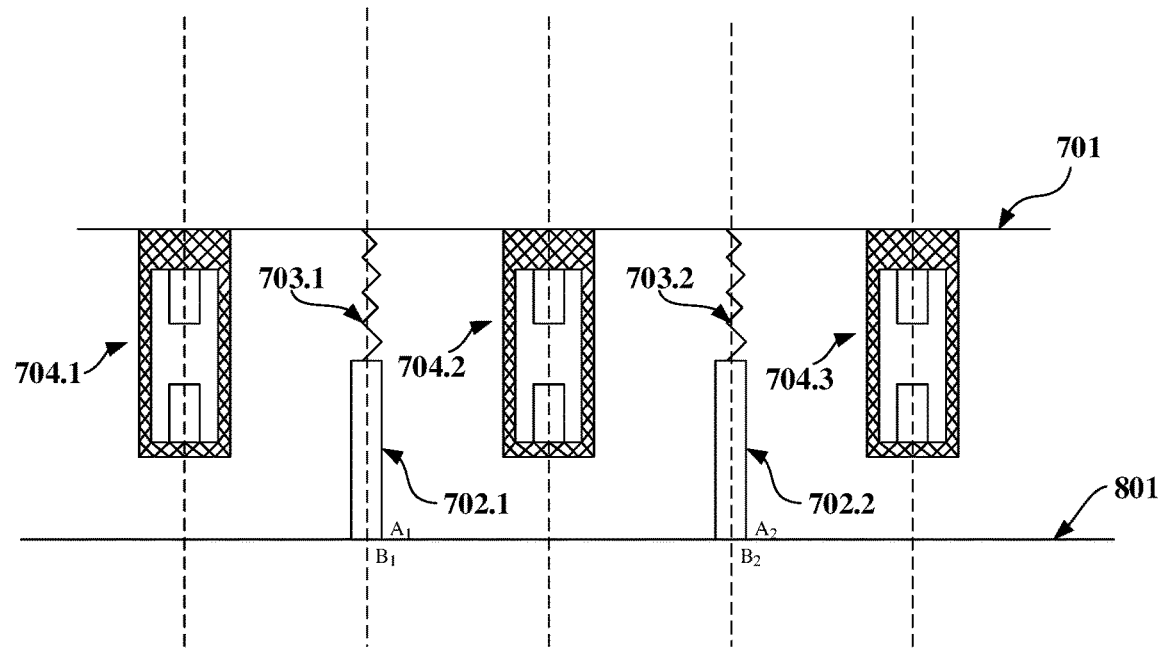
Figure 7C:
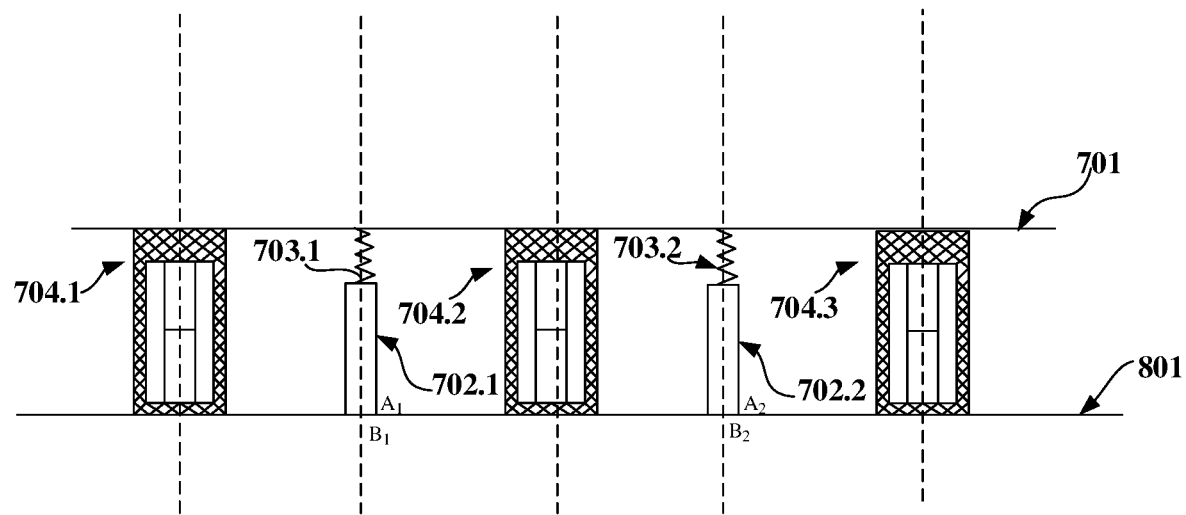

FIG. 7b and FIG. 7c illustrates the working mechanism of the device the plurality of sensor units 704 and the plurality of probe units 702, to control emission of the radiation. In an embodiment, the device may be placed on a plane surface 801 as shown in FIG. 7b. End points of the plurality of probe units 702 are indicated as points "A1" and "A2". Also, the point at which the plurality of probe units 702 may come in contact with the plane surface 801 or irregular surface may be is indicated as points "B1" and "B2". Upon placing the device on the plane surface 801, initially, the plurality of probe units 902 may come in contact with the plane surface 801. The point "A1" comes in contact with point the "B1". Similarly, at the same time the point "A2" comes in contact with point "B2". But the plurality of sensor units 704 do not touch the plane surface 801. Also, the two plates of the plurality of sensor units 704 may not be coinciding with each other.

Further, as shown in FIG. 7c, after the coincidence of the point "A1" with the point "B1" and the point "A2" with the point "B2", the points "A1" and "A2" are retracted to its maximum value of the respective elastic elements 703.1 and 703.2. The two plates of each of the plurality of sensor units 704 may come in contact with each other, when the plurality of probe units 702 are compressed on the plane surface 801 by retraction of the elastic elements 703.1 and 703.2 to maximum value of retraction. Upon maximum retraction of the elastic elements 703.1 and 703.2, the one or more sensor units 704 may come in contact with the plane surface 801. Also, the upper plate and the lower plate of the respective sensor unit from the plurality of sensor units 704 coincides with each other. Thus, upon the contact of the plurality of sensor units 704 and the plurality of probe units 702 with the plane surface 801, and upon determining first force and second force of the plurality of sensor units 704 and the plurality of probe units 702, the radiation may be emitted on the plane surface 801.

Figure 7D:
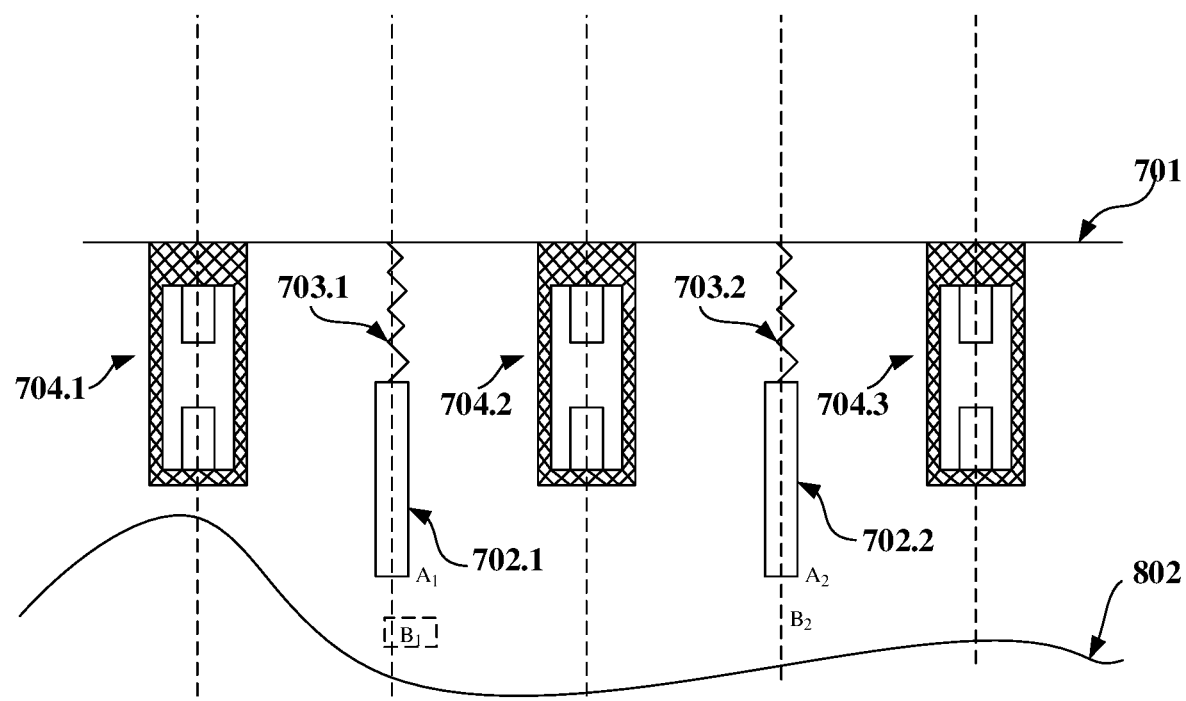

In an embodiment, the device may be placed on an irregular surface 802 as shown in FIG. 7d. The device when placed on the irregular surface 802, the sensor unit 704.1 touches the irregular surface 802. But the two plates of the sensor unit 704.1 may not coincide with each other. Also, the other sensor units 704.2 and 704.3 may not be in contact with the irregular surface 802. Similarly, the probe units 702.1 and 702.2 may also not be in contact with the irregular surface 802.

Figure 7E:
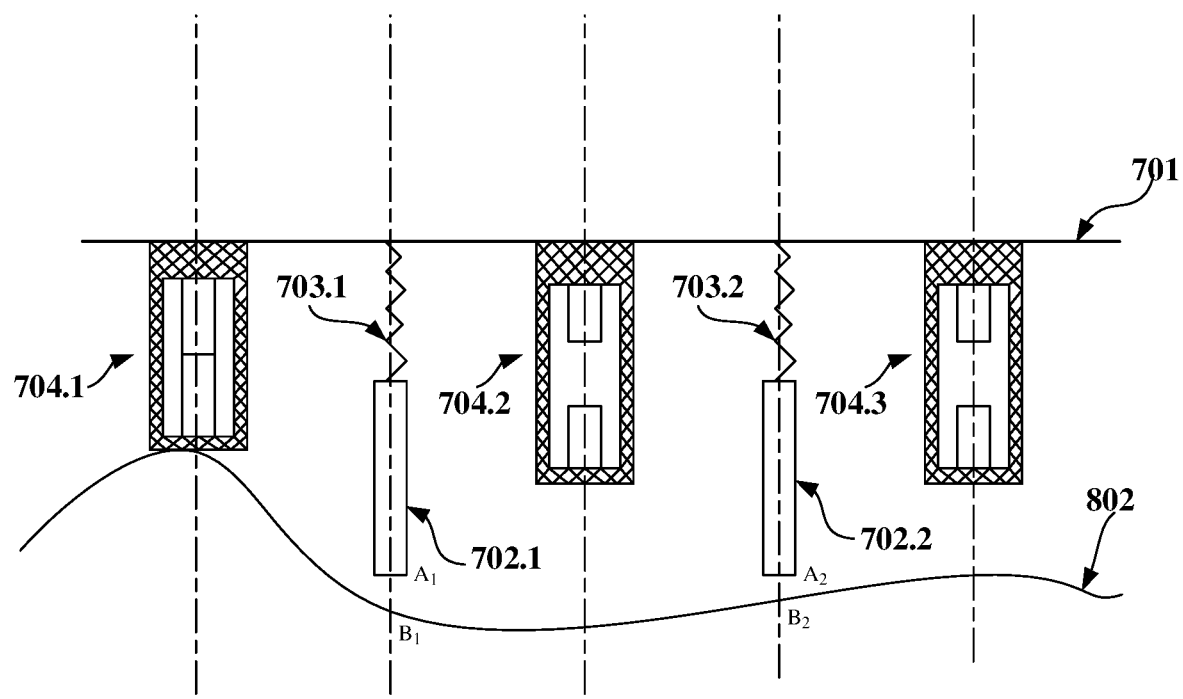

Further, the flexible material of the sensor unit 704.1 is further compressed as shown in the FIG. 7e. The flexible material of the sensor unit 704.1 is compressed by force applied externally by the operator. Upon the compression of the flexible material, the two plates of the sensor unit 704.1 coincides with each other. Also, the distance between point "A1" with point "B1" and point "A2" with point "B2" may be reduced. But the points "A1" and "A2" may not be in contact with the points "B1" and "B2", respectively.

Figure 7F:
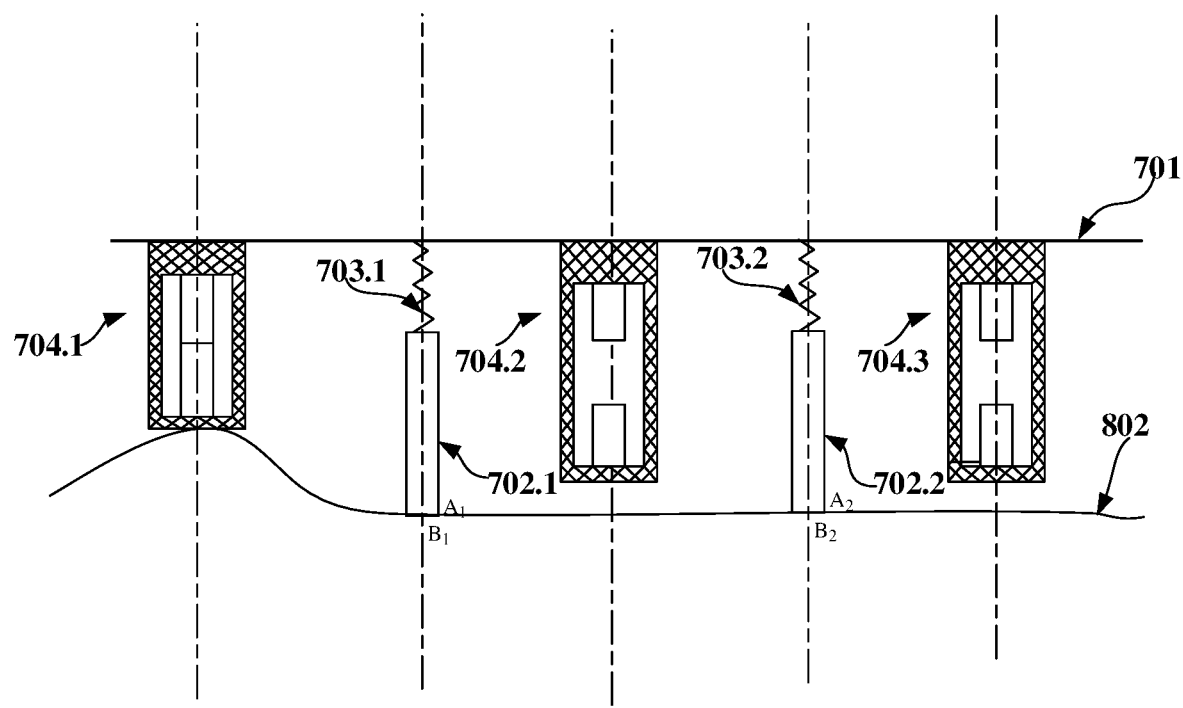

The next step as shown in FIG. 7f, the flexible material of the sensor unit 704.1 is further compressed on the irregular surface 802. Upon further compression, the flexible material of the probe units 702.1 and 702.2 may come in contact with the irregular surface 802. As a result, the point "A1" comes in contact with the point "B1" and the point "A2" comes in contact with the point "B2". Also the sensor units 704.2 and 704.3 come closer to the irregular surface 802 but does not come in contact with the irregular surface 802.

Figure 7G:
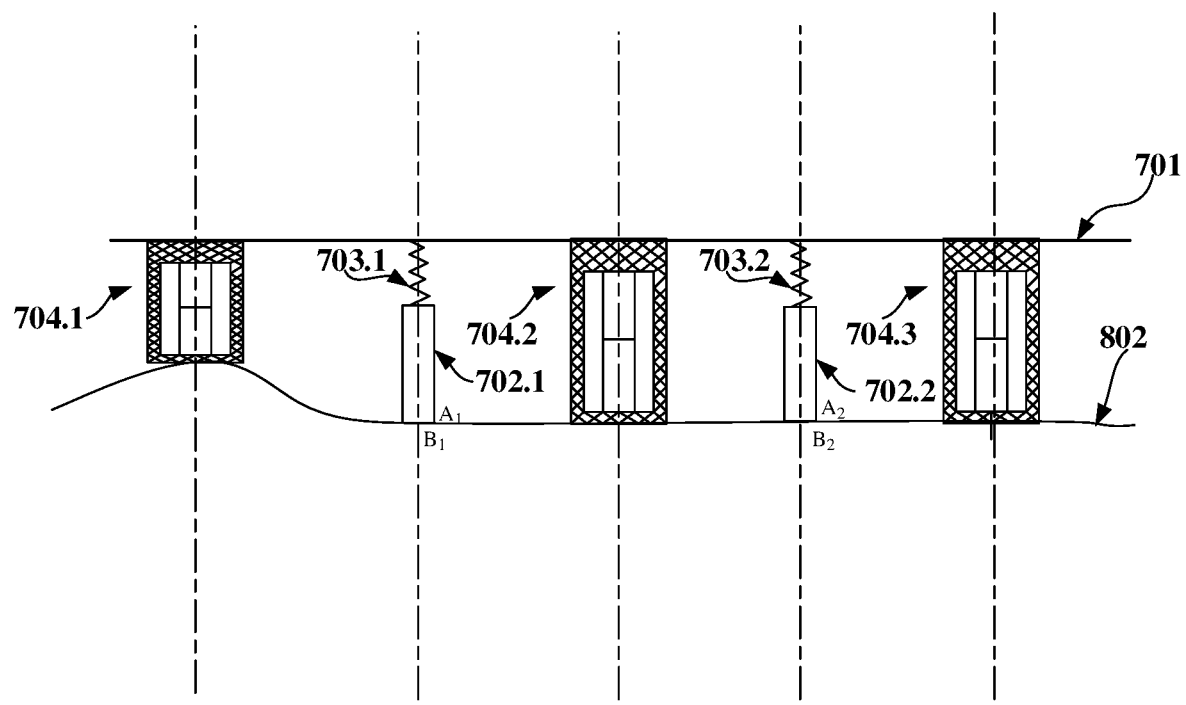

Finally, as shown in the FIG. 7g, the elastic elements 703.1 and 703.2 are compressed at the point "A1" and at the point "A2", respectively. Upon the compression, the sensor unit 704.1 is compressed further on the irregular surface 802 and also the sensor units 704.2 and 704.3 may come in contact with the irregular surface 802. The two plates of the sensor units 704.2 and 704.3 also coincide with each other. Thus, upon contact of the one or more sensor units 704 and the one or more probe units 702 on the irregular surface 802, and upon determining at least one of the first force and the second force of the plurality of sensor units 704 and the plurality of probe units 702, the radiation 105 is emitted from the one or more probe units 902.

In an embodiment, each of the plurality of probe units 702 may be associated with a respective sensor unit forming pair of sensor and probe system. In such arrangements, each of the plurality of probe units 702 may be configured to emit the radiation when contact plates of the corresponding sensor unit coincide with each other. Here, the emission from the plurality of probe units 702 may be discrete and independent from each other.

Embodiments of the present disclosure provisions to eliminate accidental exposure to radiation in a device. This is achieved by implemented mechanism where the radiation is emitted only when contact of the probe unit and sensor unit with the surface of the subject is determined.

Embodiments of the present disclosure provisions to reduce contact error.

Embodiments of the present disclosure provisions to provide power to the probe unit only upon determining contact of probe unit with the surface of the subject with sufficient force. Thus, leading in optimising power consumption in an optical device.

Embodiment of the present disclosure provisions contact based sensor unit to ensure accurate detection of contact with surface of the subject. Also, the sensor unit is protected with soft material like foam, which reduces harshness or harm caused on surface due to force on the sensor unit.

The terms "flexible" "elastic" "compressible" and so on mean to a mechanism or element or component which exhibit properties of elasticity by virtue of the material properties or design of the mechanism.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

A description of an embodiment with several components in communication with each other does not imply that all such components are required. On the contrary a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The illustrated operations of present disclosure show certain events occurring in a certain order. In alternative embodiments, certain operations may be performed in a different order, modified, or removed. Moreover, steps may be added to the above described logic and still conform to the described embodiments. Further, operations described herein may occur sequentially or certain operations may be processed in parallel. Yet further, operations may be performed by a single processing unit or by distributed processing units.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the disclosure of the embodiments of the invention is intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERRAL NUMERALS

| Reference Number | Description |
| --- | --- |
| 100a and 100b | Device |
| 101 | At least one sensor unit |
| 102 | At least one probe unit |
| 103 | At least one switch unit |
| 104 | Surface |
| 105 | Radiation |
| 106 | Power unit |
| 201 | Supporting structure |
| 202 | Elastic element |
| 203 | Flexible material |
| 204 | Cavity |
| 301a and 301b | Two plates |
| 302 | Flex sensor |
| 303 | Block |
| 304a and 304b | IR/sound sensor |
| 305 | Force sensor |
| 401 | Force sensor |
| 501 | Movable cable |

-continued

| Reference Number | Description |
| --- | --- |
| 502 | IR/sound sensor |
| 503 | Movable plate |
| 701 | Supporting structure |
| 702.1 and 702.2 | Plurality of probe units |
| 703.1 and 703.2 | Elastic elements |
| 704.1, 704.2 and 704.3 | Plurality of sensor units |
| 801 | Regular surface |
| 802 | Irregular surface |

The invention claimed is:

1. A device for controlled emission of radiation, the device comprises:
at least one probe unit configured to emit a radiation on surface of an object, wherein the at least one probe unit is supported, via an elastic mechanism, to a supporting structure of the device;
at least one sensor unit placed at a predefined distance from the at least one probe unit, along the supporting structure, to establish contact with the surface, wherein the at least one sensor unit comprises:
a flexible material, mounted to the supporting structure, with a cavity; and
a first force sensing unit placed in the cavity of the flexible material, wherein the first force sensing unit is configured to detect first force transferred from the surface to the at least one sensor unit; and
at least one switch unit configured to control emission of the radiation on the surface, based on at least one of:
the first force detected by the first force sensing unit, upon contact of the at least one sensor unit with the surface; and
identification of the at least one probe unit to be one of:
in contact with the surface of the object; and
at a minimal distance from the surface of the object.

2. The device as claimed in claim 1, wherein portion of the supporting structure supporting the at least one probe unit is of different plane with respect to portion of the supporting structure mounting the at least one sensor unit.

3. The device as claimed in claim 1, wherein the flexible material in the at least one sensor unit is configured to compress to enable transmission of the first force between the surface and the at least one sensor unit.

4. The device as claimed in claim 1, wherein the first force between the surface and the at least one sensor unit is in at least one of axial direction, transverse direction and torsional direction.

5. The device as claimed in claim 1, wherein the first force sensing unit comprises two plates placed on opposite sides of the cavity, wherein distance between the two plates decreases when the first force is transferred from the surface.

6. The device as claimed in claim 5, wherein the at least one switch unit is configured to control emission of the radiation on the surface when the distance between the two plates is zero.

7. The device as claimed in claim 1, wherein the first force sensing unit comprises:
two plates placed on opposite sides of the cavity, wherein distance between the two plates decreases when the first force is transferred from the surface; and
a flex sensor placed between the two plates, to determine flex parameter when distance between the two plates is decreased, wherein the flex parameter is directly proportional to the first force.

8. The device as claimed in claim 1, wherein the first force sensing unit comprises:
a block configured to displace when the first force is transferred from the surface; and
at least one of Infrared (IR) sensor and sound sensor to determine displacement of the block inside the cavity, wherein the displacement is directly proportional to the first force.

9. The device as claimed in claim 1, wherein the first force sensing unit comprises:
a force sensor to determine force caused due to the first force transferred from the surface, wherein the force is directly proportional to the first force.

10. The device as claimed in claim 1, wherein the at least one switch unit is configured to control emission of the radiation on the surface by detecting the first force to be greater than a first threshold value.

11. The device as claimed in claim 10, wherein the first threshold value is adjusted at least one of manually and automatically, based on one or more factors associated with the device.

12. The device as claimed in claim 1, wherein the identification of the at least one probe unit to be in contact with the surface is performed using a second force sensing unit coupled with the at least one probe unit, wherein the second force sensing unit is configured to detect a second force transferred between the surface and the at least one probe unit.

13. The device as claimed in claim 12, wherein the elastic mechanism of the at least one probe unit enables transmission of the second force between the surface and the at least one probe unit.

14. The device as claimed in claim 12, wherein the second force sensing unit is a force sensor, configured to determine force caused due to the second force transferred from the surface, wherein the force is directly proportional to the second force.

15. The device as claimed in claim 12, wherein the second force sensing unit is at least one of IR sensor and sound sensor, coupled with a movable cable in the at least one probe unit, wherein at least one of the IR sensor and the sound sensor is configured to determine displacement of the movable cable caused due to the second force transferred from the surface, wherein the displacement is directly proportional to the second force.

16. The device as claimed in claim 12, wherein the at least one switch unit is configured to control emission of the radiation on the surface by detecting the second force to be greater than a second threshold value.

17. The device as claimed in claim 16, wherein the second threshold value is adjusted at least one of manually and automatically, based on one or more factors associated with the device.

18. The device as claimed in claim 1, wherein the identification of the at least one probe unit to be at the minimal distance is performed using a proximity sensor coupled with the at least one probe unit.

19. The device as claimed in claim 1, wherein the identification of the at least one probe unit to be at the minimal distance is performed using the first force sensing unit of the at least one sensor unit.

20. The device as claimed in claim 1, wherein distance between two plates of the first force sensing unit is used to identify the at least one probe unit to be at the minimal distance.

21. The device as claimed in claim 1, wherein the minimal distance associated with the at least one probe unit and the surface of the object is derived based on radius of curvature of the surface.

22. The device as claimed in claim 1, wherein the at least one switch unit is configured to control emission of the radiation by performing at least one of:
controlling supply of power to the at least one probe unit; and
varying one or more properties of the radiation based on the first force and the identification.

23. A method of controlled emission of radiation, the method comprising:
identifying at least one probe unit of a device to be one of:
in contact with a surface of an object; and
at a minimal distance from the surface of the object, wherein the at least one probe unit is configured to emit a radiation on the surface, wherein the at least one probe unit is supported, via an elastic mechanism, to a supporting structure of the device;
detecting first force between at least one sensor unit and the surface, upon contact of the at least one sensor unit with the surface, wherein the at least one sensor unit is placed at a predefined distance from the at least one sensor unit, along the supporting structure, to establish contact with the surface, wherein the at least one sensor unit comprises:
a flexible material, mounted to the supporting structure, with a cavity; and
a first force sensing unit placed in the cavity of the flexible material, wherein the first force sensing unit is configured to detect the first force; and
controlling emission of the radiation on the surface using at least one switch unit, based on at least one of the identification and the detection.

24. The method as claimed in claim 23, wherein support provided by the supporting structure to the at least one probe unit and the at least one sensor unit is of different planes.

25. The method as claimed in claim 23, wherein transmission of the first force between the surface and the at least one sensor unit is enabled by compression of the flexible material in the at least one sensor unit.

26. The method as claimed in claim 23, wherein the first force between the surface and the at least one sensor unit is in at least one of axial direction, transverse direction and torsional direction.

27. The method as claimed in claim 23, wherein the first force sensing unit comprises two plates placed on opposite sides of the cavity, wherein distance between the two plates decreases when the first force is transferred from the surface.

28. The method as claimed in claim 27, wherein controlling of emission of the radiation by the at least one switch unit on the surface occurs when the distance between the two plates is zero.

29. The method as claimed in claim 23, wherein detecting the first force by the first force sensing unit comprises:
decreasing distance between two plates of the first force sensing unit, placed on opposite sides of the cavity, the first force is transferred from the surface; and
determining a flex parameter using a flex sensor placed between the two plates, when distance between the two plates is decreased, wherein the flex parameter is directly proportional to the first force.

30. The method as claimed in claim 23, wherein detecting the first force by the first force sensing unit comprises:
displacing a block in the first force sensing unit when the first force is transferred from the surface; and determining displacement of the block inside the cavity using at least one of Infrared (IR) sensor and sound sensor, wherein the displacement is directly proportional to the first force.

31. The method as claimed in claim 23, wherein detecting the first force by the first force sensing unit comprises:
determining force caused due to the first force transferred from the surface using a force sensor, wherein the force is directly proportional to the first force.

32. The method as claimed in claim 23, wherein controlling emission of the radiation on the surface using the at least one switch unit is performed when the first force is detected to be greater than a first threshold value.

33. The method as claimed in claim 32, further comprises adjusting the first threshold value at least one of manually and automatically, based on one or more factors associated with the device.

34. The method as claimed in claim 23, wherein the identification of the at least one probe unit to be in contact with the surface is performed using a second force sensing unit coupled with the at least one probe unit, wherein the second force sensing unit is configured to detect a second force transferred between the surface and the at least one probe unit.

35. The method as claimed in claim 34, wherein the elastic mechanism of the at least one probe unit enables transmission of the second force between the surface and the at least one probe unit.

36. The method as claimed in claim 34, wherein detecting the second force transferred between the surface and the at least one probe unit comprises determining force using a force sensor, wherein the force is directly proportional to the second force.

37. The method as claimed in claim 34, wherein detecting the second force transferred between the surface and the at least one probe unit comprises determining displacement of a movable cable in the at least one probe unit, caused due to the second force, using at least one of IR sensor and sound sensor, coupled with the movable cable, wherein the displacement is directly proportional to the second force.

38. The method as claimed in claim 34, wherein controlling of the emission of the radiation by the at least one switch unit is performed when the second force is detected to be greater than a second threshold value.

39. The method as claimed in claim 38, further comprises adjusting the second threshold value at least one of manually and automatically, based on one or more factors associated with the device.

40. The method as claimed in claim 23, wherein the identification of the at least one probe unit to be at the minimal distance is performed using a proximity sensor coupled with the at least one probe unit.

41. The method as claimed in claim 23, wherein the identification of the at least one probe unit to be at the minimal distance is performed using the first force sensing unit of the at least one sensor unit.

42. The method as claimed in claim 23, wherein distance between two plates of the first force sensing unit is used to identify the at least one probe unit to be at the minimal distance.

43. The method as claimed in claim 23, further comprises deriving value of the minimal distance associated with the at least one probe unit and the surface of the object, based on radius of curvature of the surface.

44. The method as claimed in claim 23, wherein controlling emission of the radiation using the at least one switch unit, comprises performing at least one of:
controlling supply of power to the at least one probe unit; and
varying one or more properties of the radiation based on the first force and the identification.

* * * * *